United States Patent
Kostenich et al.

(10) Patent No.: US 10,582,895 B2
(45) Date of Patent: Mar. 10, 2020

(54) METHODS AND DEVICES FOR PROVIDING INFORMATION USEFUL IN THE DIAGNOSIS OF ABNORMALITIES OF THE GASTROINTESTINAL TRACT

(71) Applicant: TEL HASHOMER MEDICAL RESEARCH INFRASTRUCTURE AND SERVICES, LTD., Ramat Gan (IL)

(72) Inventors: Genady Kostenich, Ramat Gan (IL); Arie Orenstein, Tel Aviv (IL)

(73) Assignee: TEL HASHOMER MEDICAL RESEARCH INFRASTRUCTURE AND SERVICES LTD., Ramat Gan (IL)

( * ) Notice: Subject to any disclaimer, the term of this patent is extended or adjusted under 35 U.S.C. 154(b) by 0 days.

(21) Appl. No.: 15/940,056

(22) Filed: Mar. 29, 2018

(65) Prior Publication Data
US 2018/0289330 A1    Oct. 11, 2018

Related U.S. Application Data

(63) Continuation of application No. 14/658,930, filed on Mar. 16, 2015, now abandoned, which is a continuation of application No. 13/979,863, filed as application No. PCT/IB2012/050264 on Jan. 19, 2012, now abandoned.
(Continued)

(51) Int. Cl.
*A61B 1/04* (2006.01)
*A61B 5/00* (2006.01)

(52) U.S. Cl.
CPC ........... *A61B 5/6861* (2013.01); *A61B 1/041* (2013.01); *A61B 5/0059* (2013.01); *A61B 5/0084* (2013.01); *A61B 5/42* (2013.01); *A61B 5/4255* (2013.01)

(58) Field of Classification Search
CPC ..... A61B 1/041; A61B 1/043; A61B 1/00186; A61B 1/0646; A61B 1/0676; A61B 1/0684; A61B 5/0084; A61B 5/42; A61B 5/0071; A61B 5/06; A61B 5/061; A61B 5/073;
(Continued)

(56) References Cited

U.S. PATENT DOCUMENTS 4,021,663 A * 5/1977 Takahashi .............. A61B 1/045
250/214.1
5,722,407 A 3/1998 Klingenbeck-Regn et al.
(Continued)

FOREIGN PATENT DOCUMENTS

EP    2127592 A1    12/2009
JP    2005124823 A    5/2005
(Continued)

OTHER PUBLICATIONS

International Search Report for PCT/IB2010/053539 dated Dec. 1, 2010.
(Continued)

*Primary Examiner* — Elmer M Chao
(74) *Attorney, Agent, or Firm* — Heslin Rothenberg Farley & Mesiti P.C.

(57) ABSTRACT

Ingestible devices and methods useful for providing information useful in the diagnosis of gastrointestinal abnormalities are provided.

6 Claims, 8 Drawing Sheets

Related U.S. Application Data

(60) Provisional application No. 61/434,566, filed on Jan. 20, 2011, provisional application No. 61/440,932, filed on Feb. 9, 2011.

(58) Field of Classification Search
CPC .. A61B 2018/00982; A61B 2560/0468; A61B 2562/0233; A61B 2562/162
See application file for complete search history.

(56) References Cited

U.S. PATENT DOCUMENTS

| | | | |
|---|---|---|---|
| 5,983,120 A | 11/1999 | Groner et al. | |
| 6,091,984 A | 7/2000 | Perelman et al. | |
| 6,104,939 A | 8/2000 | Groner et al. | |
| 6,912,412 B2 | 6/2005 | Georgakoudi et al. | |
| 7,282,723 B2 | 10/2007 | Schomacker et al. | |
| 7,465,271 B2 | 12/2008 | Kanazawa | |
| 7,751,039 B2 | 7/2010 | Ramanujam et al. | |
| 8,649,849 B2 | 2/2014 | Liu et al. | |
| 2002/0109774 A1 | 8/2002 | Meron et al. | |
| 2004/0092825 A1 | 5/2004 | Madar et al. | |
| 2005/0027178 A1 | 2/2005 | Iddan | |
| 2005/0154277 A1 | 7/2005 | Tang et al. | |
| 2006/0052708 A1 | 3/2006 | Iddan et al. | |
| 2007/0291247 A1 | 12/2007 | Kim et al. | |
| 2008/0119740 A1 | 5/2008 | Iddan | |
| 2009/0076396 A1 | 3/2009 | Yaroslaysky et al. | |
| 2009/0171149 A1 | 7/2009 | Segawa et al. | |
| 2009/0204009 A1 | 8/2009 | Powers et al. | |
| 2009/0270702 A1 | 10/2009 | Zeng et al. | |
| 2010/0106025 A1 | 4/2010 | Sarfaty et al. | |
| 2010/0179437 A1 | 7/2010 | Maeda et al. | |
| 2012/0259229 A1 | 10/2012 | Wang et al. | |
| 2014/0135609 A1 | 5/2014 | Kostenich et al. | |
| 2014/0343435 A2 | 11/2014 | Kostenich et al. | |
| 2015/0173623 A1 | 6/2015 | Kostenich et al. | |
| 2015/0182169 A1 | 7/2015 | Kostenich et al. | |

FOREIGN PATENT DOCUMENTS

| | | | |
|---|---|---|---|
| JP | 2006167046 A | 6/2006 | |
| JP | 2007125403 A | 5/2007 | |
| KR | 100911741 B1 | 8/2009 | |
| KR | 101746010 B1 | 6/2017 | |
| WO | 2005110186 A2 | 11/2005 | |
| WO | 2008102803 A1 | 8/2008 | |
| WO | 2012098520 A1 | 7/2012 | |

OTHER PUBLICATIONS

International Search Report for PCT/IB2012/050264 dated May 7, 2012.
Non-Final Office Action issued for U.S. Appl. No. 14/639,718, dated Jun. 25, 2018.
U.S. Appl. No. 61/434,566, filed Jan. 20, 2011.
U.S. Appl. No. 61/440,932, filed Feb. 9, 2011.

* cited by examiner

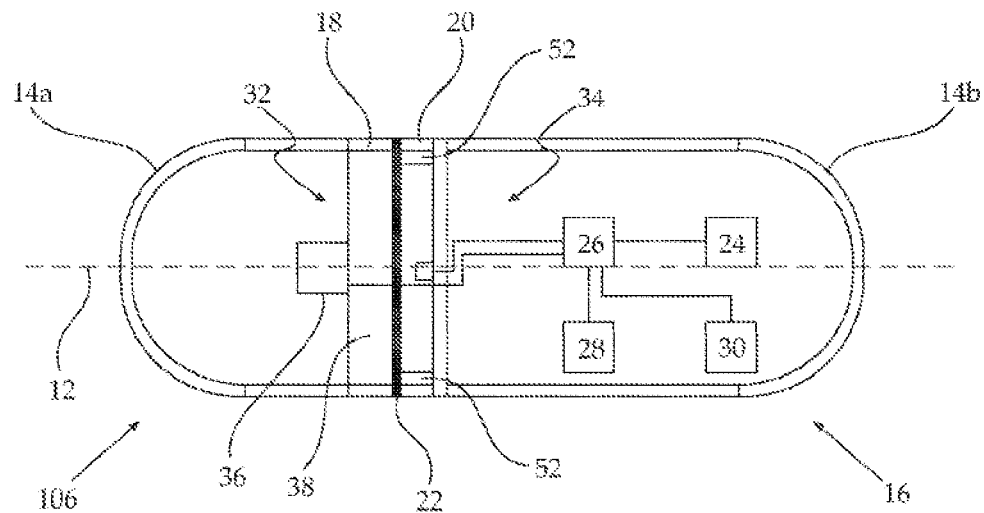
FIG. 2A
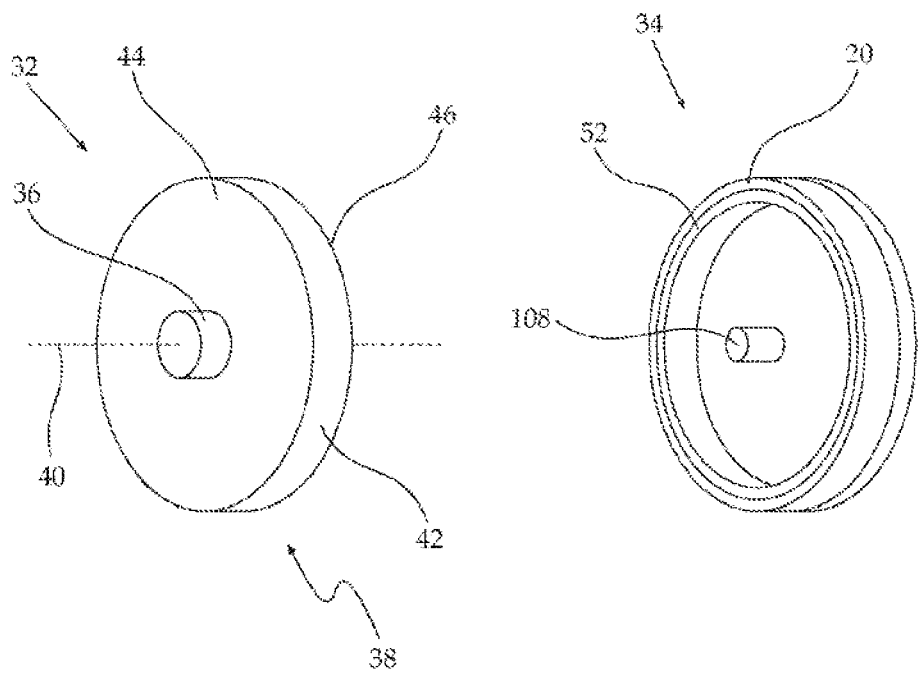
FIG. 2B
FIG. 2C

METHODS AND DEVICES FOR PROVIDING INFORMATION USEFUL IN THE DIAGNOSIS OF ABNORMALITIES OF THE GASTROINTESTINAL TRACT

RELATED APPLICATIONS

This application is a continuation of U.S. application Ser. No. 14/658,930 filed on Mar. 16, 2015, which is now abandoned and which is a continuation of U.S. application Ser. No. 13/979,863 filed on Jul. 16, 2013, which is now abandoned and which is a Section 371 national phase entry of PCT application number PCT/M2012/050264 filed on Jan. 19, 2012, and published in English on Jul. 26, 2012 as WO 2012/098520 A1, which claims priority from U.S. provisional application No. 61/434,566 filed on Jan. 20, 2011 and U.S. provisional application No. 61/440,932 filed on Feb. 9, 2011, all of which are hereby incorporated by reference as if fully set forth herein.

FIELD AND BACKGROUND OF THE INVENTION

The invention, in some embodiments, relates to the field of medical diagnosis, and more particularly but not exclusively, to methods and devices for providing information useful in the diagnosis of abnormalities of the gastrointestinal tract (gastrointestinal abnormalities).

Ingestible imaging devices for inspecting the gastrointestinal tract are known, for example the Pillcam™ available from Given Imaging (Yokneam, Israel). Such capsule-shaped devices generally include an illumination source and an imaging component (a digital camera) at one or both (distal and proximal) ends. As known in the art of digital photography, the image-acquisition portion of such a camera is a planar array of light sensitive sensors (e.g., CCD, CMOS). For use, such an imaging device is swallowed by a subject and the device is propelled through the gastrointestinal tract by peristalsis. While passing through the gastrointestinal tract, the camera acquires images of the gastrointestinal tract and wirelessly transmits the images to a recording device. The images of the gastrointestinal tract are subsequently inspected by a health care professional, as a lengthy video, for evidence of gastrointestinal abnormalities such as bleeding, polyps, cancers and lesions.

Such ingestible imaging devices have disadvantages. Ingestible imaging devices are expensive, requiring complex and expensive cameras and often requiring small moving parts such as lenses in order to acquire diagnostically-useful images. Ingestible imaging devices have high power requirements for operating the camera and an illumination source bright enough to allow acquisition of the images. The camera of such imaging devices is necessarily directed parallel to the lumen but has limited field of view of the intestinal wall where gastrointestinal abnormalities are located. Furthermore, ingestible imaging devices produce large amounts of image (video) data. As a result, data acquisition and transmission is not trivial, must be performed continuously and requires a significant amount of power. The large amount of data cannot be reviewed automatically and instead requires a time-consuming review by a skilled health-care professional, a factor that raises the cost of using such devices. Even the most highly skilled health-care professional is only able to identify relatively large abnormalities that are visible under the poor intraluminal lighting conditions so that small abnormalities and abnormalities that have certain colors often remain undetected.

It would be useful to have methods and ingestible devices that provide information useful for the diagnosis of gastrointestinal abnormalities that are devoid of at least some of the disadvantages of known ingestible imaging devices.

SUMMARY OF THE INVENTION

Some embodiments of the invention relate to methods and devices for providing information useful for the diagnosis of gastrointestinal abnormalities by determining the intensity of at least one specified wavelength of light reflected, in some embodiments diffusely reflected light, from a portion of an intestinal wall, that in some embodiments are devoid of at least some of the disadvantages of known ingestible imaging devices.

In some embodiments, the relative intensity of at least two specified wavelengths of light (diffusely) reflected from a portion of the intestinal wall is determined and provides information useful for the diagnosis of gastrointestinal abnormalities.

According to an aspect of some embodiments of the invention there is provided an ingestible device useful for providing information useful for the diagnosis of gastrointestinal abnormalities, comprising:
a) an ingestible casing having a device axis, a body section, a distal end and a proximal end;
b) inside the casing, an illuminator configured to project light radially outwards through an illuminator window of the casing substantially simultaneously in a substantially 360° circumferential section around the device axis; and
c) inside the casing, at least one light-detection assembly configured to determine the total intensity of at least one specified wavelength of light projected by the illuminator and passing through an associated detector window substantially simultaneously in a substantially 360° circumferential section around the device axis, after reflection from a substantially 360° circumferential section of a gastrointestinal tract, without acquiring an image.

According to an aspect of some embodiments of the invention there is provided a method for providing information useful for the diagnosis of gastrointestinal abnormalities, comprising:
a) illuminating an area of an in vivo gastrointestinal tract of a living mammal with light, wherein the illuminating is outwards from inside the gastrointestinal tract lumen;
b) without acquiring an image of the area, determining the total intensity of at least one specified wavelength of light after the light is reflected from the area of the gastrointestinal tract; and
c) providing information related to the intensity of light indicative of a potential gastrointestinal abnormality in the area, wherein the area is constitutes a 360° circumferential section of the gastrointestinal tract.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

BRIEF DESCRIPTION OF THE FIGURES

Some embodiments of the invention are herein described with reference to the accompanying figures. The description, together with the figures, makes apparent to a person having ordinary skill in the art how some embodiments of the invention may be practiced. The figures are for the purpose of illustrative discussion and no attempt is made to show details of an embodiment in more detail than is necessary for a fundamental understanding of the invention. For the sake of clarity, some objects depicted in the figures are not to scale.

In the Figures:

FIGS. 2A-2C are schematic depictions of an embodiment of a device as described herein configured for determining the intensity of only one specified wavelength of light;

DESCRIPTION OF SOME EMBODIMENTS OF THE INVENTION

Figure 1A:
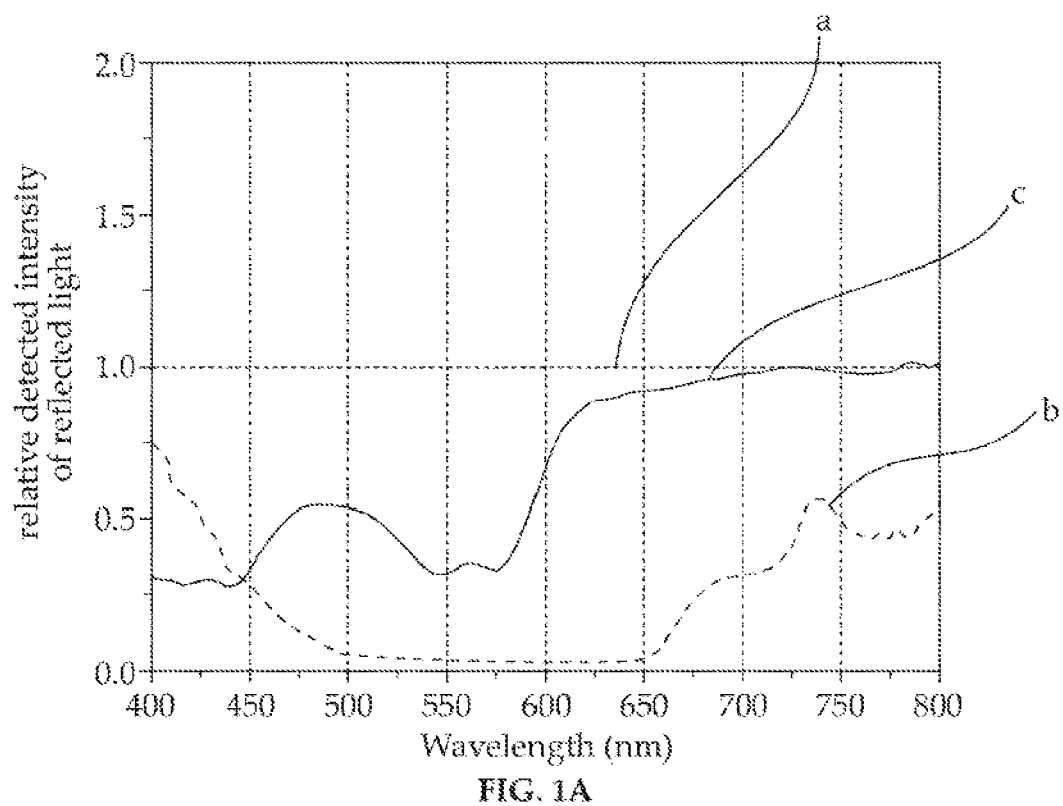
FIGS. 1A-1C depict results of experimentally-acquired spectra of normal and abnormal gastrointestinal tissue, demonstrating aspects of the teachings herein.

Some embodiments of the invention relate to methods and devices for providing information useful for the diagnosis of gastrointestinal abnormalities by determining the total intensity of at least one specified wavelength of light (diffusely) reflected from an area of the gastrointestinal tract without acquiring an image of the area, where the area constitutes a substantially 360° circumferential section of the gastrointestinal tract. The area of a gastrointestinal tract is, depending on the embodiment, any portion of a gastrointestinal tract that is downstream of the pylorus, e.g., the duodenum, small intestine or large intestine.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein.

The invention is capable of other embodiments or of being practiced or carried out in various ways. The phraseology and terminology employed herein are for descriptive purpose and should not be regarded as limiting.

Known ingestible imaging devices for inspection of the gastrointestinal tract have a 5 number of disadvantages as discussed in the introduction hereinabove.

Herein are disclosed methods and devices for providing information useful for the diagnosis of gastrointestinal abnormalities by determining the intensity of at least one specified wavelength of light (diffusely) reflected from an area of the gastrointestinal tract (e.g., intestinal wall).

To understand some embodiments of the method, one must consider the process of reflection, both diffuse reflection and specular reflection.

Some light that illuminates an area of intestinal wall penetrates into the tissue and is absorbed by chromophores in the tissue. As any given chromophore absorbs different wavelengths of light with different efficiencies and as the presence, nature and concentration of chromophores is tissue-type dependent, different tissue types absorb different wavelengths of light differently.

Light that penetrates into the tissue is also scattered inside the tissue, reflected and refracted in many directions from various features such as cells, organelles and interstitial tissue where some of the light is ultimately diffusely reflected out of the tissue back in the general direction of the illumination. The degree of scattering and diffuse reflection is dependent on the concentration, size and shape of the reflecting features as well as the refractive index of the various tissue components. Due to the ranges of refractive indices, concentrations as well as size of scattering features in gastrointestinal tissue, the degree of diffuse reflection of visible light and near-infrared light (400-800 nm) is wavelength-dependent.

It has been found and is herein disclosed that the differences of light absorption, scattering and diffuse reflection in normal compared to some abnormal gastrointestinal tissue is sufficient to provide information that can be useful for diagnosis of gastrointestinal abnormalities.

Further, for a given light-detector, the detected intensity of both specular and diffuse reflection from a tissue surface is dependent on the distance of the detector from the surface: the further a surface, the lower the intensity of reflected light independent of wavelength.

According to an aspect of some embodiments of the invention, there is provided a method for providing information useful for the diagnosis of gastrointestinal abnormalities, comprising:

a) illuminating an area of an in vivo gastrointestinal tract of a living mammal (a human or non-human mammal) with light, wherein the illuminating is outwards from inside the gastrointestinal tract lumen;

b) without acquiring an image of the area, determining an intensity of at least one specified wavelength of light after the light is (diffusely) reflected from the area of the gastrointestinal tract; and c) providing information related to the intensity of light indicative of a potential gastrointestinal abnormality in the area, for example to a person such as a health-care professional.

In some embodiments, the mammal is unsedated, preferably ambulatory, whether in a clinical or (more preferably) non-clinical setting.

In some embodiments, the intensity determined is of diffusely reflected light. In some embodiments, the intensity determined is substantially exclusively of diffusely reflected light. The provided information may then be used, alone or together with other information regarding the living mammal, to diagnose a gastrointestinal abnormality, for example bleeding, cancers, invasive adenocarcinoma, adenomas, adenomatous polyps, benign polyps and hyperplastic polyps but also other abnormalities.

In some embodiments, the provided information relates to wavelength-dependent abnormalities, that is to say, have characteristics to absorb and scatter different wavelengths of light differently. In some embodiments, the abnormalities detected are distance (from an illuminator and to a light-detection assembly) sensitive, that is to say the intensity of the reflected light changes with distance, for example polyps and other abnormalities having an abnormal shape, usually protruding into the intestinal lumen.

Thus, in some embodiments, identification of tissue as potentially abnormal is by wavelength-dependent reflection characteristics and does not require acquisition and analysis of an image as known in the art. Accordingly, some embodiments of the method described herein may be considered a form of spectroscopy. Useful background art for greater understanding some aspects of some embodiments of the method may be found, for example, in Dhar M et al, *Gastrointestinal Endoscopy* 2006, 63(2), 257.

In some embodiments, when an area of gastrointestinal tissue is illuminated with light some of the light penetrates into the tissue and undergoes both absorption and scattering. The intensity of a specified wavelength of light that is ultimately diffusely reflected and detected is tissue-type dependent. By determining an intensity of a specified wavelength of light diffusely reflected from an area of tissue and comparing the determined intensity to some reference value (e.g., an absolute value, an intensity of light having the same wavelength reflected from a different area, an intensity of light having a different wavelength reflected from the same area) it is possible to identify the area of tissue as potentially abnormal.

Figure 1B:
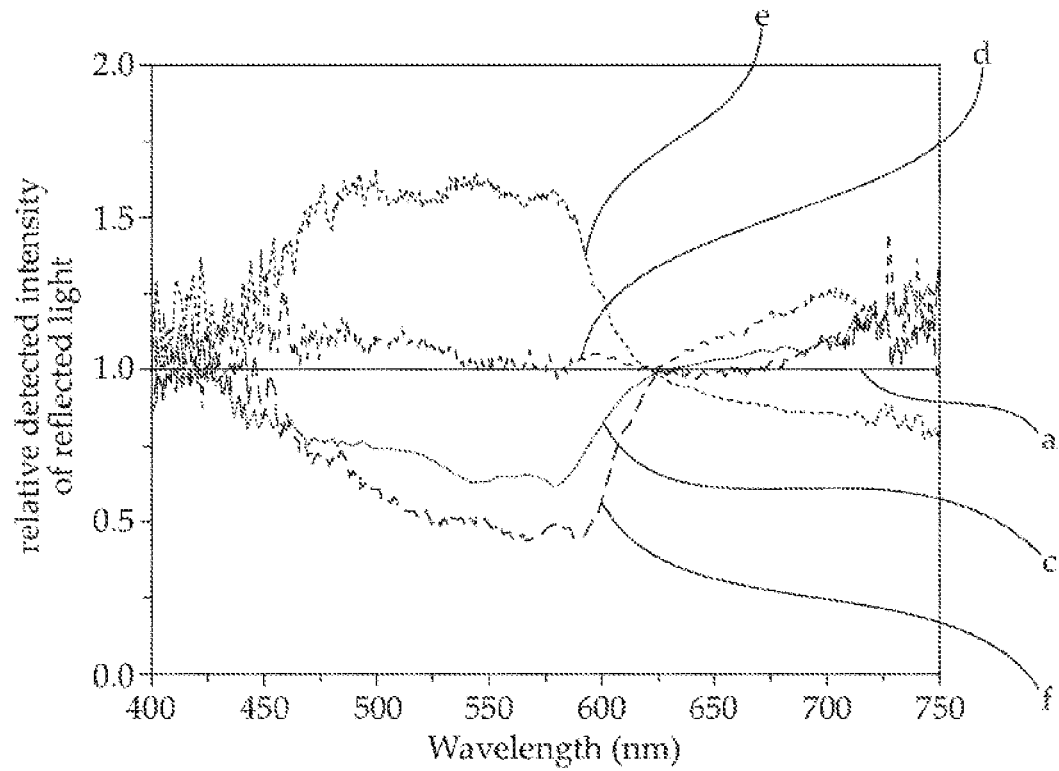
Figure 1C:
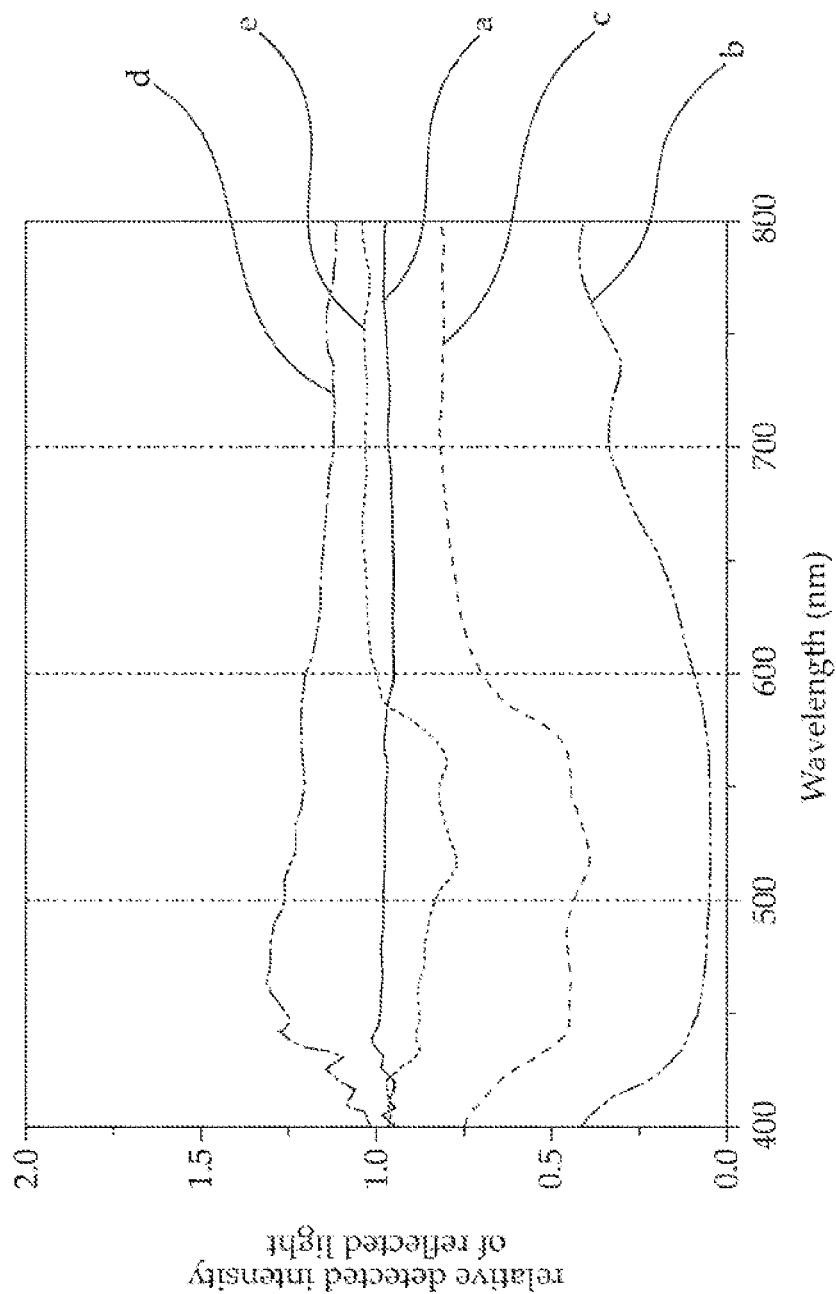

In FIGS. 1A-1C results are shown of actual experiments performed (as detailed in the Example section) on normal and abnormal gastrointestinal tissue demonstrating the wavelength and tissue-type dependence of diffuse reflection.

In a first experiment, the wavelength dependence of diffuse reflection from intestinal abnormalities relative to normal intestinal mucosa was examined in a manner simulating the use of an ingestible device as described herein on excised intestinal tissue. The results of the experiment are shown in FIG. 1A, where the relative detected intensities of light diffusely reflected from normal mucosa (plot 'a'), blood (plot 'b') and invasive adenocarcinoma (plot 'c') normalized relative to light reflected from normal mucosa at wavelengths between 400 nm and 800 nm are shown.

In a second experiment, the wavelength dependence of diffuse reflection from various intestinal abnormalities related to invasive adenocarcinoma relative to normal intestinal mucosa was examined in a manner simulating the use of an ingestible device as described herein in vivo. The results of the experiment are shown in FIG. 1B, where the relative detected intensities of light diffusely reflected from normal mucosa (plot 'a'), invasive adenocarcinoma (plot 'c'), a hyperplastic polyp (plot 'd'), an adenomatous polyp (plot 'e') and adenoma (plot 'f') normalized relative to light diffusely reflected from normal mucosa at wavelengths between 400 nm and 750 nm are shown.

In a third experiment, the wavelength dependence of diffuse reflection from various intestinal abnormalities relative to normal intestinal mucosa was examined in a manner simulating the use of an ingestible device as described herein on excised intestinal tissue. The results of the experiment are shown in FIG. 1C, where the relative detected intensities of light diffusely reflected from normal mucosa (plot 'a'), blood (plot 'b'), invasive adenocarcinoma (plot 'c'), a hyperplastic polyp (plot 'd') and adenoma (plot 'e') normalized relative to light diffusely reflected from normal mucosa at wavelengths between 400 nm and 800 nm are shown.

As apparent from FIGS. 1A-1C, different tissue types diffusely reflect light in a characteristic, identifiable and wavelength-dependent fashion so that information relating to the intensity of at least one specified wavelength of diffusely reflected light provided in accordance with the teachings herein may be useful in assisting diagnosis of some types of gastrointestinal abnormalities.

In some embodiments, at least one of the specified wavelengths is a wavelength having a high tissue-type dependent diffuse reflection for a gastrointestinal abnormality and can be considered a diagnostic wavelength for that gastrointestinal abnormality. In some embodiments, at least one of the specified wavelengths is a wavelength having a low tissue-type dependent diffuse reflection for a gastrointestinal abnormality. "Low" and "high" are qualitative terms that are easily understood by a person having ordinarily skill in the art, for example, by consulting FIGS. 1A-1C or through minor, not undue, experimentation.

For example, from FIGS. 1A-1C, it is seen that various wavelengths between 450 and 700 nm can be diagnostic wavelengths for bleeding, invasive adenocarcinomas, adenomas, and adenomatous polyps when compared to normal tissue.

In some embodiments, the intensity of at least two different specified wavelengths of light reflected from the same area is determined. The relative intensities of the reflections of the two different wavelengths are compared and, as apparent from FIGS. 1A-1C, may be indicative of abnormal tissue.

For example, a strong reduction of intensity for wavelengths between about 430 nm and about 600 nm (relative to normal tissue) when accompanied by a more moderate reduction, unchanged or increase of intensity for wavelengths between about 700 nm and about 800 nm (relative to normal tissue) may be indicative of an abnormality such as invasive adenocarcinoma but when accompanied by a strong reduction of intensity for wavelengths between about 700 nm and about 800 nm (relative to normal tissue) may be indicative of an abnormality such as bleeding.

In some such embodiments, one of the at least two specified wavelengths is diagnostic for one or more abnormalities, and another of the at least two specified wavelengths is diagnostic for at least one different abnormality.

In some such embodiments, one of the at least two specified wavelengths is diagnostic for an abnormality, and another of the at least two specified wavelengths is diagnostic for the same abnormality, providing increased confidence in a potential diagnosis.

In some such embodiments, the determination of the intensity of light of at least two specified wavelength allows comparison of the intensities of the two wavelengths to provide information useful for diagnosis.

In some such embodiments, at least one of the at least two specified wavelengths is a diagnostic wavelength (a wavelength for which intensity changes are indicative of an abnormality, e.g. 550 nm indicative of invasive adenocarcinoma) and at least one of the at least two specified wavelengths is a reference wavelength (e.g., 700 nm). Determination of the intensity of a reference wavelength allows, in some embodiments, normalization of the determined intensities of the one or more diagnostic wavelengths and, in some embodiments, allows separation of diagnostically useful measurements from not-useful measurements.

In some such embodiments, the variations in intensities are wavelength independent and indicative of the lack of contact with the intestinal wall. In some such embodiments, the intensities of the diagnostic wavelength determined during contact with the intestinal wall are separated from the intensities of the diagnostic wavelength determined with no contact with the intestinal wall with reference to the determined intensities of a reference wavelength. For example, in some embodiments, the intestinal walls physically contact a device only in the contracted portion of the peristaltic cycle. A similar magnitude of reduction in intensity of reflection of both 650 nm (reference) and 550 nm (diagnostic) wavelengths is indicative of no contact with the intestinal wall during that measurement. In contrast, a reduction in intensity of reflection of 550 nm while the intensity of reflection of 650 nm remains substantially constant is indicative of contact with the intestinal wall during that measurement with possible detection of a potential invasive adenocarcinoma.

In some embodiments, the information provided is the determined intensities. In some embodiments, the information provided is information calculated from the determined intensities, for example relative intensities, ratios and the like.

In some embodiments, the information provided is the intensity of a specified wavelength of light reflected from an area of the gastrointestinal tract compared to the intensity of light having the same specified wavelength reflected from a different area of the gastrointestinal tract. In some such embodiments, especially when the intensity of reflected light is determined from a plurality of discrete areas substantially simultaneously, differences in the tissue type in the different areas or difference in the distance to the different areas can be identified. For example, as seen from FIG. 1A, when comparing the intensity of reflection from different areas, a reduced intensity of light at 550 nm may be indicative of an abnormality such as bleeding or invasive adenocarcinoma.

In some embodiments, the information provided is a comparison of at least two (in some embodiments, exactly two or exactly three) respective intensities of at least two different specified wavelengths reflected from the same area, for example the ratio of intensities of two different wavelengths is compared, where a low ratio is indicative of normal tissue and a high ratio is indicative of abnormal tissue. In some such embodiments, the comparison reduces the influence of non-wavelength dependent variations in intensity and emphasizes the influence of wavelength-dependent variations, and is therefore useful, in some embodiments, for differentiating between different tissue types. Such wavelength intensity ratios that are significantly different (lower or higher) from those of normal tissue may be indicative of an abnormality. For example, in some embodiments the intensity of light having a wavelength of 550 nm (1550) reflected from an area is compared to that of light having a wavelength of 625 nm (1625) reflected from the same area. Intensities that are similar (1550=1625) but both lower than those of normal tissue are indicative of bleeding, a significantly higher intensity of 1625 compared to 1550 (1625>1550) is indicative of invasive adenocarcinoma or adenoma, while a significantly higher intensity of 1550 compared to 1625 (1550>1625) is indicative of adenomatous polyp of hyperplastic polyp.

In some embodiments, for example when greater detection confidence is desired (both with regards to selectivity, specificity, abnormality type) or when it is desired to seek and potentially detect more than one type of abnormality, the relative intensities of more than two wavelengths of reflected light are determined and compared (e.g., three, four, five and even more wavelengths). In some embodiments, the relative intensities of only the wavelengths to be compared are acquired. In some embodiments, the relative intensities of more than only the wavelengths to be compared are acquired. In some embodiments, the relative intensities of a plurality of wavelengths are acquired, in some embodiments constituting a spectrum. In some embodiments, the method described herein is not applied to only detecting an abnormality at one specific selected area of a gastrointestinal tract.

In some embodiments, the method described herein includes scanning the surface of the gastrointestinal tract and determining the intensity of at least one specified wavelength of light reflected from each one of a plurality of areas in succession.

In some embodiments, the method described herein includes simultaneously determining the intensity of at least one specified wavelength of light reflected from each one of a plurality of areas.

In some embodiments, the method described herein includes substantially simultaneously illuminating a plurality of discrete areas of the gastrointestinal tract. In some embodiments, the plurality of discrete areas constitutes a circumferential section of the gastrointestinal tract, in some embodiments a 360° circumferential section (a ring) of the gastrointestinal tract. In some embodiments, determining the intensity of at least one specified wavelength of reflected light is substantially simultaneous for the plurality of discrete areas. In some embodiments, the method comprises sequentially detecting light reflected from succeeding rings of tissue making up the gastrointestinal tract.

In some embodiments, the determined intensities are analyzed and reacted upon, for example a specific action is undertaken when potentially abnormal tissue is detected, e.g., an alarm is sounded, a marker or active pharmaceutical ingredient is administered.

In some embodiments, the provided information (e.g., determined intensities, relative intensities, ratios) is recorded. In some embodiments, the provided information is transmitted. In some embodiments, the provided information is transmitted continuously. In some embodiments, the provided information is transmitted intermittently (e.g., less frequently than about every minute, less frequently than about every hour), for example in order to save power. In some embodiments, a portable relay device (e.g., a cellular telephone, a personal digital assistant, a dedicated transceiver) is in proximity to the living mammal and used as a relay, continuously or intermittently receiving the provided information and subsequently retransmitting the provided information, for example to a central location such as hospital or physician. In some embodiments, the provided information is converted into an image, for example using pipe-simulation mathematics. In some embodiments, a portable recording device (e.g., a cellular telephone, a personal digital assistant, a dedicated recorder receiver) is in proximity to the living mammal and used to, continuously or intermittently receive the provided information and subsequently record the information, for example on a removable storage medium such as a memory card.

The method described herein may be implemented using any suitable device, for example, in some embodiments, a device as described herein is used to implement the method.

According to an aspect of some embodiments of the invention, there is provided an ingestible device for providing information useful for the diagnosis of gastrointestinal abnormalities, the device comprising:

a) an ingestible casing having a device axis, a body section, a distal end and a proximal end;

b) inside the casing, an illuminator configured to project light radially outwards through an illuminator window of the casing, allowing illumination a region of a gastrointestinal tract wall (e.g., intestinal wall) in which the device is passing and contacting;

c) inside the casing, at least one light-detection assembly configured to determine the intensity of at least one specified wavelength of light passing through an associated detector window without acquiring an image.

For use in accordance with some embodiments of the method discussed hereinabove, the device is ingested. After passing the pylorus, the illuminator projects light radially through the associated illuminator window that in some embodiments acts as a light guide to guide light from the illuminator out of the casing, illuminating an area of the gastrointestinal wall. The projected light is reflected back through a detector window that in some embodiments acts as a light guide to guide reflected light towards the light-detection assembly where the intensity of the specified wavelength of the reflected light is determined. As discussed above with reference to the method described herein, the intensity of at least one specified wavelength of light reflected from an area in the illuminated region may be indicative of an abnormality in the area.

In the art, ingestible gastrointestinal imaging devices include an objective, usually an adjustable objective, comprising one or more lenses and/or mirrors, that form an image of an object on a two-dimensional detector array located at the focal plane of the objective. The device described herein is used for inspection of the gastrointestinal tract without acquiring an image. In some embodiments, the inspection of the gastrointestinal tract is performed without a lens. In some embodiments, the device comprises a fixed lens to concentrate light at a light detector, but not to form an image.

It is important to note that in order to acquire an image, prior art ingestible imaging devices necessarily include a camera. The camera acquires an image of a relatively large portion of the intestinal tract, generally in parallel to the intestinal lumen. As known in the art of digital cameras, each pixel of the camera detector simultaneously acquires multiple wavelengths of light from a given area (each pixel corresponding to an area, where the areas together make up the portion of the intestinal tract of which image is being acquired). Such imaging devices need relatively long acquisition time for each image frame.

In contrast, in some embodiments of the device herein, the intensity of each specified wavelength from a given area is determined in a different physical location, e.g., a different light-detection assembly, a different region of a detector of the same light-detection assembly. Thus, in some embodiments, the device is configured to determine the intensity of at least two specified wavelengths of light each at a substantially different location. In some embodiments, the device is configured to determine the intensity of at least two specified wavelengths of light, each with a substantially different detector. In some embodiments of the device described herein, a light-detection assembly includes a simple, one-dimensional array of light sensors. Such detectors determine the intensity of each specified wavelength from a relatively small area and need a relatively short acquisition time at one physical location of the device.

Some embodiments of the devices described herein are relatively cheap, requiring simpler and cheaper components than known ingestible imaging devices.

Some embodiments of the devices described herein are relatively mechanically reliable compared to known ingestible imaging devices, requiring (substantially) no moving parts.

Some embodiments of the devices described herein have a low power consumption compared to known ingestible imaging devices (depending on the embodiment, due to, for example, less intense illumination requirements, less acquired data, no moving mechanical parts, fewer pixels per frame), requiring smaller, cheaper and less toxic power storage units, e.g., batteries.

Like prior art ingestible imaging devices, the casing of a device is generally configured for passage, once swallowed by a mammalian subject and passing the pylorus, for transport through the gastrointestinal tract for eventual expulsion through the anus where either the distal or proximal end faces forwards, where the device axis is substantially parallel to the gastrointestinal tract lumen and where the gastrointestinal walls physically contacts the body section to propel the device by peristalsis.

In some embodiments, the body section includes a substantially parallel-walled cylindrical portion where the walls of the body section are parallel to the device axis.

In some embodiments, the distal end and/or the proximal end are streamlined for passage of the device through the gastrointestinal tract.

In some embodiments, the device comprises inside the casing a power supply for providing substantially all power for operation of the device once ingested until expelled. In some embodiments, when compared to a power supply required for known ingestible imaging devices, the power supply is relatively modest as the device has relatively lower power requirement as there is no need for imaging, no moving parts, less intense illumination, and per unit time, less data to transmit and/or record.

In some embodiments, the device comprises inside the casing, a processor, for example configured to compare the determined intensities of specified wavelengths of light.

In some embodiments, the device comprises inside the casing, a wireless transmitter for transmitting information related to the determined intensities of the specified wavelengths, such as the determined intensity of the specified wavelengths or results of comparison of the determined intensities of the specified wavelengths. In some embodiments, the wireless transmitter is, like in known ingestible imaging devices, configured for continuous transmission of the information. In some embodiments, the wireless transmitter is configured for non-continuous (e.g., intermittent or periodic) transmission of the information, in order to reduce interference potentially caused by transmission, to reduce exposure of a subject ingesting the device to radiation, and to reduce power use by the device. In some embodiments, non-continuous transmission is possible because the device does not acquire images, but only modest amounts of information. In some embodiments, the information is transmitted only over a short range (e.g., to a device carried by the subject such as a dedicated device, a cellular telephone, a personal digital assistant) and stored and/or retransmitted.

In some embodiments, the device comprises inside the casing, a memory for recording information related to the determined intensities of the specified wavelength, for example, the device includes a solid-state memory component or a removable solid-state memory component such as a micro-SD card. In some embodiments, the recorded information is substantially all the information useful for the diagnosis of abnormalities in the gastrointestinal tract determined during passage through a gastrointestinal tract. In some embodiments, recording of substantially all the useful information is possible because the device does not acquire images, but only relatively modest amounts of information.

An illuminator of a device described herein is configured to project light including one or more specified wavelengths, typically between about 400 nm and 800 nm. In some embodiments, an illuminator is configured to project monochromatic light. In some embodiments, an illuminator is configured to project polychromatic or white light that includes the specified wavelengths of light.

In some embodiments, the illuminator comprises a light source for producing light having the specified wavelengths. Any suitable light source may be used, for example a light-emitting diode. In some embodiments, such a light source is configured for producing monochromatic light. In some embodiments, such a light source is configured for producing polychromatic light. In some embodiments, such a light source is configured for producing white light. In some embodiments, the illuminator comprises a light source for producing light having wavelengths between 400 and 800 nm.

In some embodiments, a light source comprises a radial diffuser functionally associated with the light source for radially distributing light produced by the light source.

The illuminator and the illuminator window are configured together to project light in any suitable direction. In some embodiments, the illuminator and illuminator window are configured together to project light substantially perpendicularly to the device axis. In some embodiments, the illuminator and illuminator window are configured together to project light at an angle different than 90° to the device axis, e.g., in a direction towards or away from a detector window, in some embodiments not more than 10° from perpendicular to the device axis and in some embodiments not more than 5° from perpendicular to the device axis.

The illuminator is configured to project light radially allowing illumination of any shaped region of a gastrointestinal lumen. In some embodiments, the illuminator is configured to project light in circumferential section of at least about 90°, at least about 120°, and even at least about 180° at one time around the device axis, allowing substantially simultaneous illumination of an equivalent circumferential section of gastrointestinal lumen. That said, in preferred embodiments, the illuminator is configured to project light in a circumferential section that is substantially the entire 360° around the device axis, allowing substantially simultaneous illumination of substantially a 360° circumferential section (a ring) of gastrointestinal tissue.

The illuminator window through which the illuminator projects light is substantially transparent to at least the specified wavelengths. An illuminator window is of any suitable shape and construction, and is generally fashioned of glass or plastic material as known in the art of ingestible imaging devices. In some embodiments, an illuminator window is made up of two or more discrete parts assembled so that the illuminator window is continuous. In some embodiments, an illuminator window is made up of two or more discrete parts assembled where at least two of the parts are separated by a non-transparent component. That said, it is generally preferred (for reasons of ease of construction as well as to reduce the chance of leakage of gastrointestinal fluids into the casing) that the illuminator window comprises substantially a single discrete component. In some embodiments, a radial diffuser constitutes the illuminator window.

In some embodiments, the illuminator and the illuminator window together are configured that the projected light is polarized, for example, the illuminator window is a light polarization component or the illuminator comprises a light polarization component.

In some embodiments where the illuminator is configured to project light in a certain circumferential section (e.g., 120°), the illuminator window comprises an arc or disk section of at least the same circumferential section of a material substantially transparent to light having the specified wavelengths. In some embodiments, especially where the illuminator is configured to project light in a substantially 360° circumferential section, the illuminator window is a ring or a disk of a material substantially transparent to light having the specified wavelengths, in some embodiments positioned coaxial with the device axis.

A light-detection assembly of a device described herein is configured to determine the intensity of at least one specified wavelength of light passing through an associated detector window. As discussed above, specified wavelengths are typically between about 400 nm and 800 nm.

In some embodiments, a device is configured to determine the intensity of at least two specified wavelengths of light each at a substantially different (physical) location. In some embodiments, a device is configured to determine the intensity of at least two specified wavelengths of light each with a substantially different light-detection assembly. In some embodiments, a device is configured to determine the intensity of at least two specified wavelengths of light at substantially different locations of the same light-detection assembly. In some embodiments, a light-detection assembly and associated detector window comprise at least one wavelength filter configured to pass only light having a specified wavelength of light. In some embodiments, a wavelength filter is functionally associated with a detector window. In some embodiments, a wavelength filter is a component of or is a detector window.

In some embodiments, a light-detection assembly and an associated detector window are configured so that light reaching the light-detection assembly is polarized, for example, the illuminator window is a light polarization component or the light-detection assembly comprises another light polarization component. In some such embodiments, the light polarization component associated with the light-detection assembly is oriented perpendicularly to the light polarization component associated with the illuminator. Such cross polarization reduces specular reflection and allows more selective acquisition of substantially only diffusely reflected light.

In some embodiments, a device comprises a single light-detection assembly.

In some embodiments, a device comprises at least two light detection assemblies. In some such embodiments, the device comprises at least one detector window associated with at least two of the detection assemblies. In some such embodiments, each light-detection assembly is associated with a single dedicated detector window.

In some embodiments, at least one light-detection assembly is configured to determine the intensity of one specified wavelength of light. In some such embodiments, the light-detection assembly is functionally associated with a wavelength filter that limits the wavelengths of light that reach the light-detection assembly. In some embodiments, the wavelength filter is a component of or is the detector window.

In some embodiments, at least one light-detection assembly is configured to determine the intensity of at least two specified wavelengths of light.

In some such embodiments, the light-detection assembly configured to determine the intensity of at least two specified wavelengths of light is associated with at least two detector windows. In some such embodiments, each detector window is associated with a wavelength filter each passing light having a different specified wavelength.

In some such embodiments, the light-detection assembly configured to determine the intensity of at least two specified wavelengths of light is associated with a single detector window. In some such embodiments, the detector window is associated with the appropriate number of different wavelength filters, each passing light having a different specified wavelength.

The rate of determining the intensities of the specified wavelengths of light is any suitable rate. A higher rate produces more data (determined intensities) that must be analyzed and/or transmitted and/or stored but yields greater axial resolution by determining intensities at a greater rate as the device passes through the gastrointestinal tract. Considering the speed at which peristalsis drives an ingested device through the gastrointestinal tract, it is currently believed that a rate of between 1 Hz and 20 Hz is preferred. Thus, in some embodiments, a light-detection assembly is configured to determine the intensity of the at least one specified wavelength of light at a rate of at least about 0.1 Hz, at least about 0.5 Hz and even at least about 1 Hz, preferably so that during the period of time that a device passes through the gastrointestinal tract substantially the entire luminal surface of a portion or the entire gastrointestinal tract downstream of the pylorus has been scanned.

Depending on the embodiments, a light-detection assembly can be configured to determine the intensity of at least one specified wavelength of light from any suitable direction and from any suitably-shaped region of a gastrointestinal wall.

In some embodiments, a light-detection assembly is configured to determine the intensity of light of at least one specified wavelength of light passing through an associated detector window from a circumferential section around the device axis of at least about 90°, at least about 120°, and even at least about 180° around the device axis, allowing simultaneous determination of intensities from an equivalent circumferential section (an arc-shaped region) of gastrointestinal luminal surface. That said, in preferred embodiments, a light-detection assembly is configured to determine the intensity of light in a circumferential section that is substantially the entire 360° around the device axis substantially simultaneously, allowing simultaneous determination of the intensity of reflection of substantially a 360° circumferential section (a ring-shaped region) of gastrointestinal tissue.

A detector window associated with a light-detection assembly allows light reflected from a given region of the gastrointestinal tract to reach the light-detection assembly. In some embodiments, the light-detection assembly is configured to determine the intensity of light from a single area that is substantially the entire region. For example, in some embodiments a device including a 360° circular detector window, light is reflected from a 360° ring-shaped region of the intestinal wall which is one area for which the intensity of reflected light is determined.

That said, in some embodiments, to provide additional information for diagnosis, for example, the location of an abnormality, the size of an abnormality or identification of multiple abnormalities at the same portion of the gastrointestinal tract, at least one light-detection assembly is configured to determine the intensity of at least one the specified wavelength of light passing through the associated detector window from at least two different areas, at least three, at least four, at least eight, at least ten, at least 15, at least 30, and even at least 60 different areas, for example, by an arrangement of a required number of light sensors in appropriate positions across from an associated detector window. For example, in some embodiments a device including a 360° circular detector window, a 360° ring-shaped region of the intestinal luminal wall is divided into two areas corresponding to two 180° sectors from which the intensity of light is independently determined, divided into three different areas corresponding to three 120° sectors, divided into four different area corresponding to four 90° sectors and the so on. In some such embodiments, the light-detection assembly comprises a pixelated light-detector array for determining the intensity of light from the different areas, the detector array comprising at least as many pixels as different areas. In some embodiments, a plurality of pixels are combined as a group to determine the intensity of light from one area. Any suitable technology of pixelated light-detector array may be used, e.g., monochrome pixelated arrays, CCD (charge-coupled device) arrays, PD (photo diode) arrays, CMOS (complementary metal oxide) arrays and LED (light-emitting diode) arrays.

In this context, it is important to note that to acquire images having a diagnostically-useful resolution, known ingestible imaging devices generally acquire a frame made up of at least 10000 discrete areas (pixels), usually at least 1 million discrete areas (pixels). In contrast, a device as described herein is generally configured to simultaneously determine the intensity of not more than 1000, not more than 360 and even not more than 120 discrete areas at any one time. An advantage of such a seemingly low spatial resolution is that much less intense illumination light can be used (saving power), less data is acquired and still allowing detection of abnormalities.

In some embodiments, a light-detection assembly comprises a focusing component to concentrate light entering an associated detector window onto the pixelated light-detector array. In some embodiments, a focusing element is a component of or is the detector window. In some embodiments, the apertures of the light detecting elements (pixels) of the light-detector array face an associated detector window. In some embodiments, a pixelated light-detector array has a circular periphery around which outwardly-facing light-detecting elements are arranged, in some such embodiments, so that the apertures of the light-detecting elements face the associated detector window.

In some embodiments, a light-detection assembly comprises a light-director to change the direction of light passing through an associated detector window towards a light-detector array. In some such embodiments, the light-detector array is substantially planar. Any suitable light-director may be used including a reflecting element (e.g., a mirror such as a substantially conical-section mirror), a light-guide, a prism, or a reflecting diffraction grating (e.g., a substantially conical-section diffraction grating).

In some embodiments, a light-director also functions as a wavelength separator (e.g., a prism (e.g., a conical section prism), a diffraction grating), in order to direct at least one specified wavelength of light towards a desired location of a light-detector array.

A detector window through which light passes to a light-detection assembly is substantially transparent to at least one of the specified wavelengths. As noted above, in some embodiments, a detector window is configured to act as a wavelength filter, for example is transparent to substantially only a single specified wavelength. As noted above, in some embodiments, a detector window is configured to act as a polarization light filter. A detector window is of any suitable shape and construction, and is generally fashioned of glass or plastic material as known in the art of ingestible imaging devices. In some embodiments, a detector window is made up of two or more discrete parts assembled so that the detector window is continuous. In some embodiments, a detector window is made up of two or more discrete parts assembled where at least two of the parts are separated by a non-transparent component. That said, it is generally preferred (for reasons of ease of construction as well as to reduce the chance of leakage of gastrointestinal fluids into the casing) that a detector window comprises substantially a single discrete component.

In some embodiments where a light-detection assembly is configured to determine the intensity of light from a certain circumferential section (e.g., 120°), the associated detector window comprises an arc or disk section of at least the same circumferential section of a material substantially transparent to at least one specified wavelength. In some embodiments, especially where an associated light-detection assembly is configured to determine the intensity of light from a substantially 360° circumferential section, the associated detector window is a ring or a disk of a material substantially transparent to at least one specified wavelength, in some embodiments positioned coaxial with the device axis.

In some embodiments, it is desired that one or more light-detection assemblies selectively detect substantially exclusively diffusely reflected light.

As noted above, in some such embodiments, the illuminator is functionally associated with a polarization component oriented in a first direction and a light-detection assembly is associated with a polarization component oriented perpendicularly to the first direction.

In some embodiments, the angular aperture of an illuminator in the plane of the device axis is relatively small so that little if any specular reflected light is detected by a light-detection assembly. In some embodiments, the angular aperture of the illuminator in the plane of the device axis is less than about 30°, less than about 20°, less than about 10° and even less than about 5°. In some embodiments, the angular aperture of an illuminator in the plane of the device axis is limited by a lens (in some embodiments, the lens constituting the illuminator window) having the desired limited angular aperture. In some embodiments, the device comprises a narrow slit substantially perpendicular to the device axis in which the illuminator and/or the illuminator window are recessed and through which light must pass, thereby limiting the angular aperture of the illuminator in the plane of the device axis.

In some embodiments, the angular aperture of a light-detection assembly in the plane of the device axis is relatively small so that little if any specular reflected light is detected by a light-detection assembly. In some embodiments, the angular aperture of the light-detection assembly in the plane of the device axis is less than about 30°, less than about 20°, less than about 10° and even less than about 5°. In some embodiments, the angular aperture of a light-detection assembly in the plane of the device axis is limited by a lens (in some embodiments, the lens constituting the associated detector window) having the desired limited angular aperture. In some embodiments, the device comprises a narrow slit substantially perpendicular to the device axis in which the light-detection assembly and/or the associated detection window are recessed and through which light must pass, thereby limiting the angular aperture of the light-detection assembly in the plane of the device axis.

In some embodiments, a light-detection assembly is functionally associated with a collimator so that light detected by the light-detection assembly first must pass the collimator, ensuring that little if any specular reflected light is detected by the light-detection assembly. In some embodiments, a collimator is a separate component. In some embodiments, a detector window is configured to also function as a collimator.

Design, construction, assembly and use of a device as described herein are apparent to a person having ordinary skill in the art upon perusal of the description and figures. Methods, materials and dimensions are similar to those used in the art of ingestible imaging devices such as the Pillcam™ (Given Imaging, Yokneam, Israel) and are easily modified to implement the teachings herein if necessary.

The dimensions of a device as described herein are any suitable dimensions, allowing passage through the gastrointestinal tract with causing excessive discomfort.

That said, in some typical embodiments, a device has a total axial length of between about 15 mm and 35 mm, between about 20 mm and 30 mm, and even 25 mm like the Pillcam™.

In some typical embodiments, a body section of a device has an axial length of between about 10 mm and 30 mm, between about 10 mm and 20 mm, and even 15 mm like the Pillcam™.

In some typical embodiments, a body section is substantially cylindrical with a diameter of between about 5 mm and 20 mm, between about 7 mm and 15 mm, and even 10 mm like the Pillcam™.

The axial dimensions (axial length) and distance between the illuminator window and the detector window are any suitable values.

An illuminator window is of any suitable axial length, but typically not more than about 5 mm. Typically, an illuminator window is not less than about 0.3 mm long not less than about 0.5 mm long, and even not less than about 1 mm long.

A detector window is of any suitable axial length, but typically not more than about 4 mm long, not more than about 3 mm, not more than about 2 mm, and even not more than about 1 mm long.

In some embodiments, in order to collect sufficient light diffusely reflected from gastrointestinal tissue, the distance from an illuminator window to a detector window is as small as possible and in some embodiments, not more than about 5 mm, not more than about 4 mm, not more than about 3 mm, not more than about 2 mm and even not more than about 1 mm. Accordingly, in embodiments with multiple detector windows on the same side of an illumination window, the detector windows tend to have a small axial length (e.g., less than about 2 mm, less than about 1 mm) and to be close together, even substantially abutting.

As discussed above, the specified wavelength or wavelengths selected for implementing a device of method as discussed herein are selected to be diagnostic for some abnormality.

The spectral width of a specified wavelength is any suitable spectral width.

As understood from the discussion above (inter alia, FIG. 1), in some embodiments a suitable spectral width is very broad, for example, in some embodiments a specified wavelength has a spectral width of: up to about 400 nm (e.g., spans from about 400 nm to about 800 nm diagnostic for bleeding, FIG. 1A);

up to about 250 nm (e.g., spans from about 400 nm to about 650 nm diagnostic for bleeding, or from about 400 nm to about 625 nm diagnostic for invasive adenocarcinoma, FIG. 1A);

up to about 150 nm (e.g., spans from about 450 nm to about 600 nm diagnostic for adenomatous polyp or adenoma, FIG. 1B, for invasive adenocarcinoma, FIG. 1A, or hyperplastic polyp FIG. 1C or spans from about 500 nm to about 650 nm diagnostic for bleeding, FIG. 1A);

up to about 125 nm (e.g., spans from about 450 nm to 575 nm, diagnostic for invasive adenocarcinoma, or spans from about 500 nm to 625 nm, diagnostic for bleeding, FIG. 1A);

up to about 100 nm (e.g., spans from about 450 nm to 555 nm, diagnostic for invasive adenocarcinoma, or spans from about 500 nm to 600 nm, diagnostic for bleeding, FIG. 1A);

up to about 75 nm (e.g., spans from about 500 nm to 575 nm, diagnostic for bleeding, FIG. 1A); or even up to about 50 nm (e.g., spans from about 525 nm to 575 nm, diagnostic for invasive adenocarcinoma, FIG. 1A or adenomatous polyp, FIG. 1B)

An advantage of such broad spectral widths is that the illuminator can be configured to produce a relatively low intensity of light, reducing energy use. A disadvantage of such broad spectral widths is the possibility that extraneous light (e.g., from external sources) will be detected as well as technical difficulty in implementing such broad spectral widths.

Thus, in some embodiments, a suitable spectral width is narrow, for example not more than about 10 nm FWHM, not more than about 5 nm FWHM and even not more than about 2 nm FWHM.

Such narrow spectral widths are technically simple to implement using commercially-available wavelength filters.

A device as described herein may include any suitable illuminator. In some embodiments, it is preferred to use an illuminator of the invention. According to an aspect of some embodiments of the invention, there is provided an illuminator useful for projecting light in a radially-outwards direction in a 360° circumferential section comprising:
a) a light source for projecting light; and
b) a radial diffuser having a diffuser axis, a first face, a second face and a substantially circular circumferential outer edge coaxial with the central diffuser axis, wherein the light source is configured to project the light into the radial diffuser; and
wherein at least a portion of the light projected into the radial diffuser from the light source radiates radially-outwards through the circumferential edge of the radial diffuser.

In some embodiments, the radial diffuser is disk-shaped, wherein at least a portion of the first face of the radial diffuser is substantially transparent to light projected by the light source; and wherein the light source is configured to project light into the radial diffuser through the transparent portion of the first face of the radial diffuser. In some such embodiments, the light source contacts the transparent portion of the first face of the radial diffuser.

In some embodiments, the radial diffuser is ring-shaped including a central hole with an inner rim; at least a portion of the inner rim is transparent to light projected by the light source; and wherein the light source is configured to project light into the radial diffuser through the inner rim. In some such embodiments, the light source contacts the transparent portion of the inner rim.

In some embodiments, the circumferential edge of the radial diffuser is perpendicular to the diffuser axis so that radially-outwards radiating light radiates substantially perpendicularly to the diffuser axis.

In some embodiments, the circumferential edge is oriented at an angle to the diffuser axis so that radially-outwards radiating light radiates at an angle relative to the diffuser axis. In some embodiments, at least a portion of the first diffuser face is opaque to light projected by the light source. In some embodiments, substantially all of the first diffuser face is opaque to light projected by the light source. In some embodiments, at least a portion of the first diffuser face is light reflecting (e.g., mirrored).

In some embodiments, at least a portion of the second diffuser face is light reflecting (e.g., mirrored). In some embodiments, at least a portion of the second diffuser face is opaque to light projected by the light source. In some embodiments with a ring-shaped diffuser, substantially all of the second diffuser face is opaque to light projected by the light source.

As noted above, in some embodiments a device described herein comprises a light-detection assembly comprises a light-director to change the direction of light passing through an associated detector window towards a light-detector array and also to function as a wavelength separator. In some such embodiments, the light-director is a reflecting diffraction grating. In such embodiments, any suitable reflecting diffraction grating may be used. In some embodiments, it is preferred to use a diffraction grating of the invention. According to an aspect of some embodiments of the invention, there is provided a diffraction grating, comprising:

a substantially conical-section surface having an axis; and on the surface, periodic features wherein the surface and the periodic features are configured to reflect light impinging substantially perpendicularly to the axis at a wavelength-dependent angle in the general direction of the axis so that the diffraction grating functions as a dispersive element. In some embodiments, the periodic features comprise ring-shaped features coaxial to the axis. In some embodiments, the features comprise ring-shaped slits in the conical surface. In some embodiments, the features comprise ring-shaped ridges on the conical surface. In some embodiments, the surface has a substantially conical shape. In some embodiments, the diffraction grating has a substantially truncated conical shape.

In some embodiments, there is provided a method for providing information useful for the diagnosis of gastrointestinal abnormalities, comprising:
a) illuminating an area of an in vivo gastrointestinal tract of a living mammal with light, wherein the illuminating is outwards from inside the gastrointestinal tract lumen;
b) without acquiring an image of the area, determining the total intensity of at least one specified wavelength of light after the light is reflected from the area of the gastrointestinal tract; and
c) providing information related to the intensity of light indicative of a potential gastrointestinal abnormality in the area, wherein the area constitutes a substantially 360° circumferential section of the gastrointestinal tract. As in some embodiments described above, the reflected light is substantially diffusely reflected light. Different from some of the embodiments discussed above, such embodiments are characterized in that for each one of at least one specified wavelengths of light a total intensity of light reflected from a substantially 360° circumferential section of the gastrointestinal tract is determined, that is to say that each 360° circumferential section of the gastrointestinal tract is examined as a whole without resolving the circumferential section into individual sectors. Although some such embodiments potentially provide less information relating to the size and exact location of a gastrointestinal abnormality, such embodiments produce an exceptionally modest volume of data and are thus useful for screening subjects, whether high-risk subjects or just members of a normal population. In some embodiments, subjects for which the method provides evidence indicative of a gastrointestinal abnormality are subject to invasive but accurate examination, such as with an endoscope.

In some such embodiments, the information provided is a comparison of at least two respective intensities of at least two different specified wavelengths of light reflected from the same area of the gastrointestinal tract, the substantially 360° circumferential section of the gastrointestinal tract.

In some embodiments, the information provided is the intensity of at least one specified wavelength of light after the light is reflected from the area (the substantially 360° circumferential section of the gastrointestinal tract) compared to an intensity of light of a same specified wavelength after the light has been reflected from a different area of the gastrointestinal tract, in some embodiments, a different substantially 360° circumferential section of the gastrointestinal tract.

Any suitable device may be used in implementing the method, for example some embodiments of devices as described hereinabove. In some embodiments it is preferred to implement the method using an exceptionally simple device that does not differentiate between intensities of light of a specified wavelength coming from different directions.

Thus, in some embodiments there is provided an ingestible device useful for providing information useful for the diagnosis of gastrointestinal abnormalities, comprising:
a) an ingestible casing having a device axis, a body section, a distal end and a proximal end (e.g., a casing as described above);
b) inside said casing, an illuminator configured to project light radially outwards through an illuminator window of said casing substantially simultaneously in a substantially 360° circumferential section around said device axis (e.g., an illuminator as described above); and
c) inside said casing, at least one light-detection assembly configured to determine the total intensity of at least one specified wavelength of light projected by said illuminator and passing through an associated detector window substantially simultaneously in a substantially 360° circumferential section around said device axis, after reflection from a substantially 360° circumferential section of a gastrointestinal tract without acquiring an image.

In some embodiments, at least one said light-detection assembly and associated said detector window comprises at least one wavelength filter configured to pass only light having a said specified wavelength of light.

In some embodiments, the device comprises a single light-detection assembly.

In some embodiments, the device comprises at least two light detection assemblies.

In some embodiments, at least one light-detection assembly is configured to determine the intensity of one specified wavelength of light.

In some embodiments, at least one light-detection assembly is configured to determine the intensity of at least two specified wavelengths of light.

In some embodiments, the device is configured to determine the intensity of at least two specified wavelengths of light each at a substantially different location in the device, e.g., a different light-detection assembly or a different location of a same light-detection assembly. In some embodiments, the device is configured to determine the intensity of at least two specified wavelengths of light each with a substantially different light-detection assembly.

In FIGS. 2A-2C, an embodiment 106 of an ingestible device is schematically depicted, in FIG. 2A device 106 in side cross-section, in FIG. 2B a detailed view of an illuminator of device 106 and in FIG. 2C a detailed view of a light-detection assembly of device 106. Device 106 is similar in dimensions and construction to a commercially available Pillcam™ (Given Imaging, Yoqneam, Israel).

The casing of device 106 includes a device axis 12, streamlined distal and proximal ends 14a and 14b and a parallel-walled cylindrical body section 16. The casing of device 106 is opaque to light except for illuminator window 18 and detector window 20, both 1 mm long complete rings of polycarbonate transparent to wavelengths of light between 400 nm and 800 nm, separated by separator 22, a 0.2 mm disk of opaque reflective foil, e.g. aluminum.

Illuminator window 18 is configured to act as a polarizing component to polarize light in parallel to device axis 12. Detector window 20 is configured to act as a polarizing component to polarize light perpendicularly to device axis 12.

Inside body section 16 are a power supply 24 (e.g., a battery), a controller 26 (e.g., an integrated circuit also configured as a processor to process acquired data), a writeable memory 28 (e.g., a micro-SD card), a wireless transmitter 30 (e.g., a Bluetooth® transceiver), an illuminator 32 and a single light-detection assembly 34.

Illuminator 32 is configured to project light radially outwards through illuminator window 18 simultaneously in a 360° circumferential section around and perpendicular to axis 12. Illuminator 32, see FIG. 2B, comprises a light source 36 (e.g., in some embodiments an LED for producing white-light, in some embodiments producing polychromatic light such as a phosphor-based white LED, in some embodiments producing specified monochromatic light (e.g., 500 nm, 515 nm, 530 nm, 545 nm light, available from Super Bright LEDs Inc., St. Louis. Mo., USA) that receives electrical power for operation from power supply 24 through controller 26 and a radial diffuser 38, which is a disk of transparent material including a diffuser axis 40 and having a circular outer edge 42 parallel to diffuser axis 40. Radial diffuser 38 is configured to radially distribute light produced by light source 36 around diffuser axis 40 where the radially-outwardly radiating light radiates substantially perpendicularly to axis 40. A portion of a first face 44 of radial diffuser 38 where light source 36 contacts first face 44 is transparent to light produced by light source 36 so that light source 36 projects light into radial diffuser 38 through the transparent portion. The other portions of first face 44 as well as an entire surface of a second face 46 of radial diffuser 38 are completely mirrored (e.g., by deposition of a layer of silver or aluminum) and therefore opaque to light.

When activated, for example by controller 26, light source 36 produces light that enters radial diffuser 38 through the transparent portion of first face 44. The produced light is reflected inside radial diffuser 38 between the mirrored portions of first face 44 and second face 46 to emerge perpendicularly to diffuser axis 40 through outer edge 42 of radial diffuser 38 and through illuminator window 18, projecting a ring of light around device 106.

Light-detection assembly 34 of device 106 is associated with detector window 20 and is configured to determine the total intensity of a single specified wavelength of light (e.g., 500 nm) passing through detector window 20 from an entire 360° circumferential section around axis 12. Light-detection assembly 34, see FIG. 2C, comprises a single light detecting element 108 (e.g., an LED such as available from Super Bright LEDs Inc., St. Louis. Mo., USA suitable for detecting light having a wavelength of 500 nm).

Intimately contacting the inner surface of detector window 20 is a ring of a narrow pass wavelength filter 50 chosen to selectively pass 500 nm light. Wavelength filter 50 is any suitable wavelength filter, for example a flexible filter available from Lee Filters, Andover, Hampshire, England.

Light-detection assembly 34 is functionally associated with controller 26, where the output of light detecting element 108 corresponding to the total intensity of light having a wavelength of 500 nm passing through detector window 20 is input for controller 26.

When light produced by illuminator 32 is reflected from intestinal tissue towards detector window 20, only light having the specified wavelength of 500 nm passing through detector window 20 passes through wavelength filter 52 to impinge on light-detecting element 108. At a rate of 10 Hz, controller 26 receives the intensity of 500 nm determined from light-detecting element 108.

For use, device 106 is activated and ingested by a subject, eventually passing the pylorus to enter and pass through the duodenum, small intestine, large intestine and rectum before being expelled through the anus. The location of the device in the gastrointestinal tract at any time is monitored in the usual way. In some embodiments, the location of the device in the gastrointestinal tract is not monitored.

Figure 3:
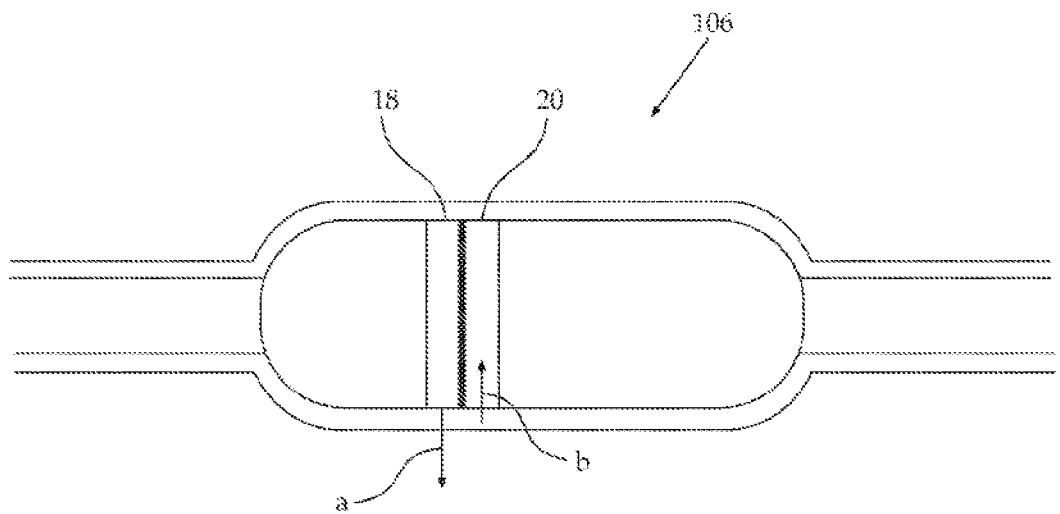
FIG. 3 is a schematic depiction of the device of FIG. 2 in use inside a gastrointestinal tract.

Illuminator 32 projects a ring of polarized light perpendicularly from illuminator window 18, illuminating a 360° circumferential section of gastrointestinal tissue in close proximity or touching illuminator window 18, arrow "a" in FIG. 3.

Some of the light is reflected from the gastrointestinal tissue towards detector window 20, arrow "b" in FIG. 3. Light reflected from a 360° circumferential section of gastrointestinal tissue of the specified wavelength (500 nm) passes through wavelength filter 52 to light-detecting element 108. If present, most specular reflected light is prevented from passing through detector window 20 due to the cross polarization between illuminator window 18 and detector window 20 so that primarily diffusely projected light reaches light-detecting element 108. The total intensity of reflected light of the specified wavelength is determined at a rate of 10 Hz. Thus, the total intensity of light of the specified wavelength passing through wavelength filter 52 that is reflected by a complete ring of tissue encircling device 106 is detected by light-detecting element 108 at a rate of 10 Hz and is reported to controller 26.

For each intensity (variable name intensity) received from light-detecting element 108, controller 26 functions as a processor to calculate and store the average intensity of detected light as a variable average in memory 28. For each intensity received from light-detecting element 108 after the tenth intensity, controller 26 calculates the intensity relative to the average intensity (relativeintensity=intensity/average). The values of relativeintensity are stored as a function of time in an array in memory 28. The determined intensities are received by controller 26 and stored in an array in memory 28. When device 106 is expelled from the anus, the device 106 is recovered and the recorded relative intensities constituting information indicative of a potential gastrointestinal abnormality can be downloaded for review and analysis to assist a medical professional in deciding whether there is an abnormality in the gastrointestinal tract of the subject.

Concurrently, controller 26 transmits the instantaneously determined values of average, intensity and relativeintensity that constitute information indicative of a potential gastrointestinal abnormality to an appropriately-configured external unit (not depicted) outside of the body through wireless transmitter 30. An automatic program (e.g., written in Fortran programming language and running on a standard general purpose computer) analyzes the received values of relativeintensity to identify a relative intensity that is sufficiently low (e.g., less than about 60%, less than about 50%, less than about 30%) of the average, indicating a potential abnormality (e.g., bleeding, invasive adenocarcinoma).

If no sufficiently low relative intensity value is identified, a medical professional may decide (optionally, together with other information) that there is sufficient evidence that the examined subject is clear of any potential gastrointestinal abnormality and take no further immediate action.

If a sufficiently low relative intensity value is identified, a medical professional may decide (optionally, together with other information) that there is sufficient evidence that the examined subject requires further examination and order a more invasive and/or more expensive procedure such as the use of a Pillcam™ (Given Imaging, Yokneam, Israel) or endoscopy (such as sigmoidoscopy, colonoscopy, enteroscopy and esophagogastroduodenoscopy).

In some embodiments, the transmitted information is analyzed in real-time, and whenever a sufficiently low relative intensity is detected, the external unit sounds an audible alarm to warn an attending health-care professional.

Figure 2D:
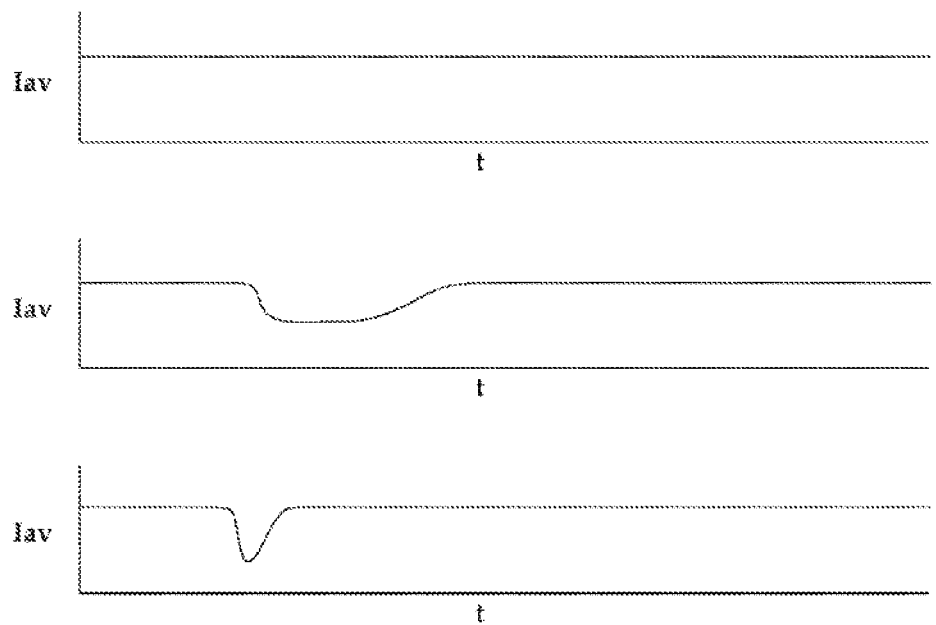
FIG. 2D depicts typical information acquired using a device depicted in FIG. 2A.

In FIGS. 2D and 2E exemplary information acquired by a device such as device 106 is depicted.

In FIG. 2D, the relative intensity of light (determined as described above) having a wavelength of 500 nm reflected from gastrointestinal tissue and detected by a light detector 108 is plotted as a function of time.

In the upper plot, device 106 passes through normal gastrointestinal tissue so the determined relative intensity is substantially constant.

In the middle plot, device 106 passes through normal gastrointestinal tissue until encountering a bleeding lesion. At the bleeding lesion and downstream therefrom for a significant length of the gastrointestinal tract, the determined relative intensity is substantially lower than of normal tissue due to the presence of blood that reduces the intensity of light having a wavelength of 500 nm that is reflected from the gastrointestinal tract to be detected by light-detection assembly 34 of device 106 as discussed above with reference to FIG. 1.

At some point in the intestine, the amount of blood on the intestinal surface becomes substantially lower and the average determined relative intensity returns to normal.

In the lower plot, device 106 passes through normal gastrointestinal tissue until encountering a localized invasive adenocarcinoma. The determined relative intensity at the invasive adenocarcinoma is substantially lower than of normal tissue as discussed above with reference to FIG. 1. When detector window 20 passes the invasive adenocarcinoma, the determined relative intensity returns to normal.

The information such as depicted in FIG. 2D acquired in accordance with embodiments of the method and device described herein, when provided to a person such as a physician can be useful in helping making a diagnosis as to the presence and nature of gastrointestinal abnormalities. For example, together with other medical data, whether the subject is likely healthy, has intestinal bleeding or invasive adenocarcinoma.

It is important to note that although device 106 is specifically configured to determine the intensity of a very narrow selected wavelength (500 nm), other wavelengths can be used (as seen from FIGS. 1A-1C), as well as much broader selected wavelengths. For example, in some embodiments for detecting bleeding, illuminator 32 is configured to project monochromatic light with specified wavelength bandwidth, polychromatic light at specified wavelength range or white light and light-detection assembly 34 is configured to determine the intensity of a selected wavelength that spans from 400 nm to 800 nm without discrimination (useful for detecting bleeding). Analogously, some embodiments useful for detecting bleeding are configured to determine the intensity of a selected wavelength that spans from 500 nm to 650 nm, and any sub-group of selected wavelengths. Analogously, some embodiments useful for detecting invasive adenocarcinoma are configured to determine the intensity of a selected wavelength that spans from 400 nm to 600 nm, and any sub-group of selected wavelengths. Analogously, some embodiments useful for detecting adenomas or adenomatous polyps are configured to determine the intensity of a selected wavelength that spans from 475 nm to 575 nm, and any sub-group of selected wavelengths.

Figure 4A:
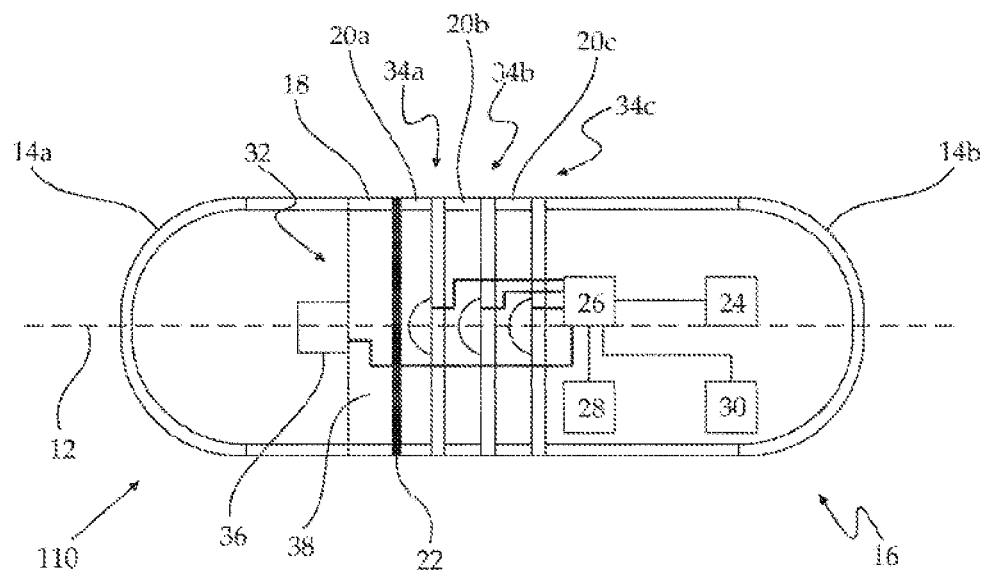
FIGS. 4A-4B are schematic depictions of embodiments of a device as described herein configured for determining the intensity of three specified wavelength of light with three light-detection assemblies.
Figure 4B:
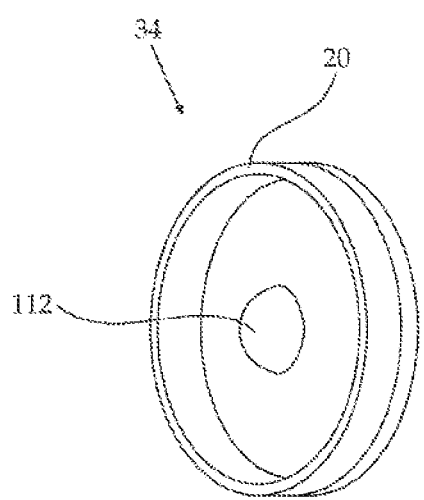

In FIGS. 4A-4B, an embodiment 110 of an ingestible device is schematically depicted: in FIG. 4A in side cross-section and in FIG. 4B a detailed view of a light detection assembly 34. Device 110 comprises multiple light-detection assemblies each configured to determine the intensity of a single specified wavelengths of light.

Device 110 comprises an illuminator 32 substantially identical to illuminator 32 of device 106 configured to project light radially outwards through illuminator window 18 in a 360° circumferential section around and perpendicular to axis 12.

Device 110 is similar to device 106 discussed above with a number of notable differences.

Whereas device 106 comprises a single light-detection assembly 34, device 110 comprises three independent light-detection assemblies 34a, 34b and 34c, each associated with a dedicated detector window 20a, 20b and 20c respectively. Light-detection assemblies 34 of device 110 are substantially similar to light-detection assembly 34 of device 106. However, instead of including a separate wavelength filter 52 as in device 106, each detector window 20 is fashioned of a colored polycarbonate material, thereby functioning as a wavelength filter so that each light-detection assembly 34 is configured to determine the intensity of a single specified wavelength of light, specifically, 500 nm (34a), 550 nm (34b) and 650 nm (34c). Consequently, device 110 is configured to determine the intensity of three specified wavelengths of light at substantially different physical locations, the respective light-detector arrays of the different light-detection assemblies 34a, 34b and 34c.

Instead of a single light-detecting diode 108 as in device 106, in device 110 each light-detection assembly 34 includes a pixelated planar light-detection array (e.g., CCD, PD, CMOS, LED such as known in the art of digital photography) that in FIG. 4B is hidden from view by a miniature fish-eye lens 112. Each fish-eye lens 112 gathers light entering a respective detector window 20 and focuses the light on a respective light-detection assembly. Although each pixel of light-detection assembly is able to determine a detected light intensity independently of the other pixels, in device 110 the outputs of all the pixels are summed and sent as a single intensity value as input for controller 26.

For use, device 110 is activated and ingested by a subject, eventually passing the pylorus to enter and pass through the duodenum, small intestine, large intestine and rectum before being expelled through the anus. The location of the device in the gastrointestinal tract at any time is monitored in the usual way. In some embodiments, the location of the device in the gastrointestinal tract is not monitored.

Illuminator 32 projects a ring of polarized light perpendicularly from illuminator window 18, illuminating a 360° circumferential section of gastrointestinal tissue in close proximity or touching illuminator window 18.

Some of the projected light is diffusely reflected from gastrointestinal tissue towards detector windows 20a, 20b and 20c. Light reflected from a 360° circumferential section of gastrointestinal tissue of the first specified wavelength (500 nm) passes through detector window 20a associated with light-detection assembly 34a. Light reflected from a 360° circumferential section of gastrointestinal tissue of the second specified wavelength (550 nm) passes through detector window 20b associated with light-detection assembly 34b. Light reflected from a 360° circumferential section of gastrointestinal tissue of the third specified wavelength (650 nm) passes through detector window 20c associated with light-detection assembly 34c. Specularly reflected light is prevented from passing through detector windows 20 due to the cross polarization between illuminator window 18 and detector windows 20 so that primarily diffusely projected light reaches the light-detector arrays. The total intensity of reflected light of the three specified wavelengths of light is determined at a rate of 10 Hz. Thus, the total intensity of light of the three specified wavelengths passing through detector windows 20 that is reflected by a complete ring of tissue encircling device 110 is detected by the light-detectors of light detection assemblies 34 at a rate of 10 Hz and are all three reported to controller 26.

The determined intensities are received by controller 26. Controller 26 functions as a processor to compare the intensities of the three different specified wavelengths reflected from the same area of the gastrointestinal tract. Specifically, for each cycle where the intensities are determined, controller 26 compares (e.g., by calculating a ratio) the intensities of 500 nm light, 550 nm light and of 650 nm light reflected from the same area. The comparisons of intensities constituting information indicative of a potential gastrointestinal abnormality are then transmitted to an appropriately-configured external unit (not depicted) outside of the body through wireless transmitter 30. An automatic program analyzes the received compared intensities (in some embodiments in real time, in some embodiments not in real time) to identify information indicative of a potential abnormality.

By comparing the determined intensities of light at the different specified wavelengths 500 nm 550 nm and 650 nm reflected from the same area of an intestinal wall, various gastrointestinal abnormalities can be potentially identified. For example, substantially similar intensities of light having wavelengths of 500 nm, 550 nm and/or 650 nm that is significantly lower than that of normal tissue is indicative of bleeding, while the pattern of an intensity of 650 nm greater than at 500 nm greater than at 550 nm is indicative of invasive adenocarcinoma, FIG. 1A. For example, intensities of 500 nm and 550 nm higher than at 650 nm are indicative of adenomatous polyp while intensities of 500 nm and 550 nm lower than of 650 nm are indicative of invasive adenocarcinoma, FIG. 1B.

Figure 4C:
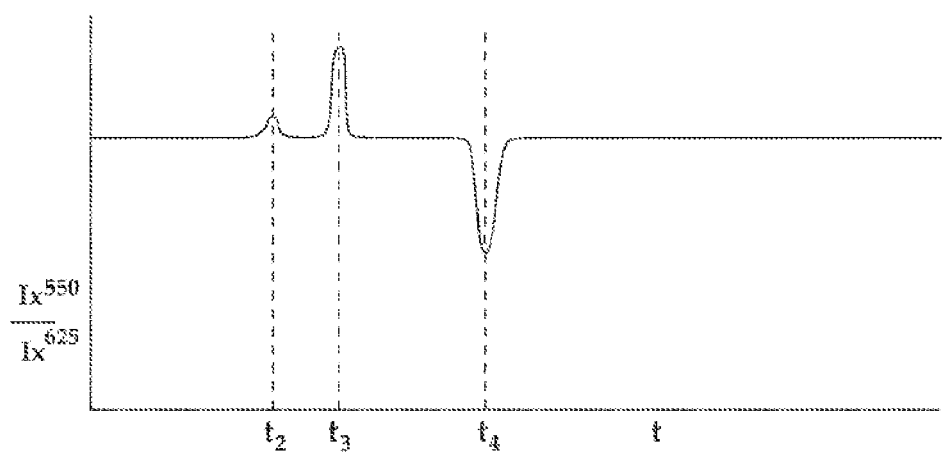
FIG. 4C depicts typical information acquired using a device depicted in FIG. 4A.

A medical professional receives the provided information and can then (based on the information, optionally together with other information) choose to do nothing or order a more invasive and/or more expensive procedure for further examination In FIG. 4C exemplary information acquired by a device such as device 110 is depicted.

In FIG. 4C, the ratio of the intensity of light having a wavelength of 550 nm) ($I_x^{550°}$) to light having a wavelength of 650 nm ($I_x^{650°}$) determined by light-detection assemblies 34b and 34c reflected from the same area X of gastrointestinal tissue is plotted as a function of time.

At time t2, a slight increase of ($I_x^{550°}$)/($I_x^{650°}$) indicates the potential presence of a hyperplastic polyp (see FIG. 1B). At time t3, a significant increase of ($I^{x550)/ox650}$,) indicates the potential presence of an adenomatous polyp (see FIG. 1B).

At time t4, a significant decrease of ($I_x^{550°}$)/($I_x^{650°}$) indicates the potential presence of a invasive adenocarcinoma (see FIG. 1B).

The information such as depicted in FIG. 4C acquired in accordance with embodiments of the method and device described herein, when provided to a person such as a physician can be useful in helping making a diagnosis as to the presence and nature of gastrointestinal abnormalities.

Figure 5A:
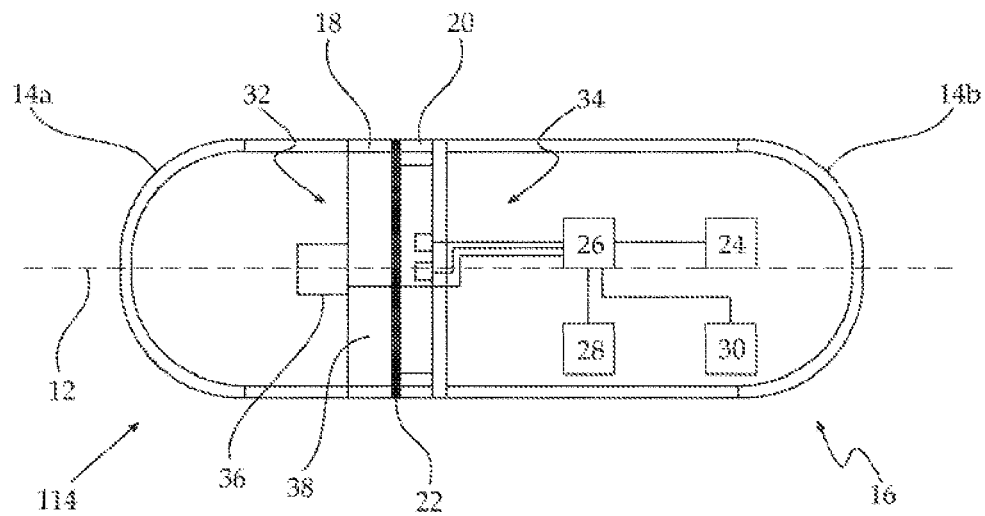
FIGS. 5A and 5B are schematic depictions of an embodiment of a device as described herein configured for determining the intensity of three specified wavelength of light with a single light-detection assembly.
Figure 5B:
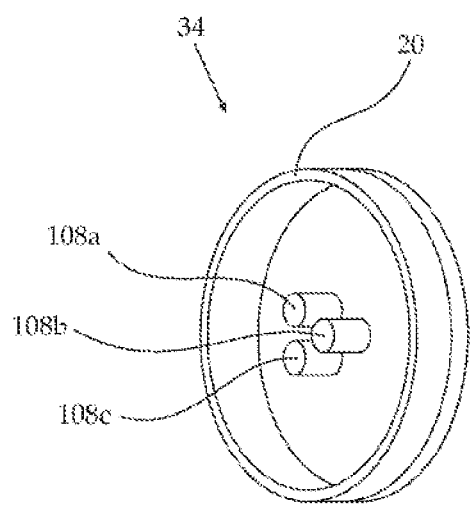

An embodiment 114 of an ingestible device is schematically depicted in FIG. 5A in side cross-section and in FIG. 5B a detailed view of a light-detection assembly 34. Device 114 comprises a single light-detection assembly configured to determine the intensity of multiple specified wavelengths of light. Device 114 is similar to devices 106 and 110 discussed above with a number of notable differences.

Device 114 comprises a single light-detection assembly 34 configured to determine the intensity of three selected wavelengths of light. Light-detection assembly 34 includes three separate light-detecting elements 108a, 108b and 108c each substantially similar to light-detecting element 108 of device 110, except that each element 108 is configured to detect the intensity of a single wavelength of light (e.g., are LED configured to determine an intensity of a specific wavelength of light or are covered with a wavelength filter) and provide a determined intensity to controller 26. Specifically, light-detecting element 108a is configured to determine the intensity of light having a wavelength of 500 nm, light-detecting element 108b is configured to determine the intensity of light having a wavelength of 550 nm and light-detecting element 108c is configured to determine the intensity of light having a wavelength of 650 nm. Consequently, device 114 is configured to determine the intensity of three specified wavelengths of light at substantially different physical locations, light-detecting elements 108a, 108b and 108c.

Device 114 is devoid of a wavelength filter 52 associated with detector window 20.

Device 114 comprises an illuminator 32 substantially identical to illuminator 32 of device 108 configured to project light radially outwards through illuminator window 18 in a 360° circumferential section around and perpendicular to axis 12.

The use of device 114 is substantially as described above with reference to device 110.

Figure 6A:
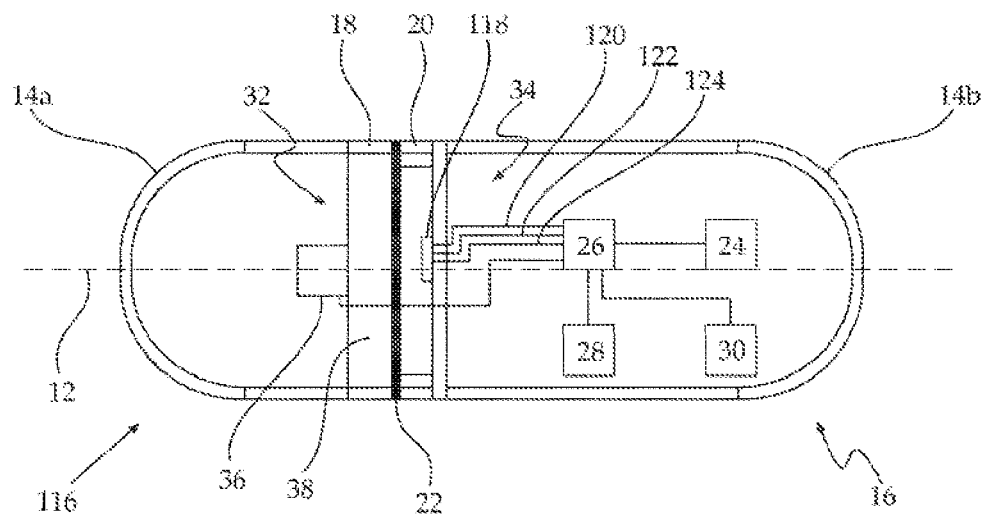
FIGS. 6A and 6B are schematic depictions of an embodiment of a device as described herein configured for determining the intensity of three specified wavelengths of light with a single light-detection assembly.
Figure 6B:
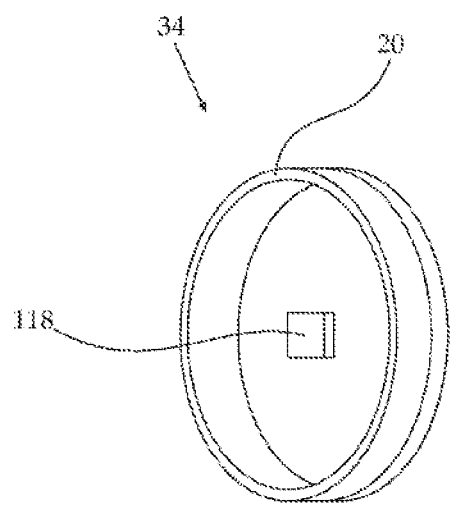

An embodiment 116 of an ingestible device is schematically depicted in FIG. 6A in side cross-section and in FIG. 6B, a detailed view of a light-detection assembly 34. Device 116 comprises a single light-detection assembly configured to determine the intensity of multiple specified wavelengths of light. Device 116 is similar to devices 106, 110 and 114 discussed above with a number of notable differences.

Device 116 comprises a single multicolor light-detection assembly 34 configured to determine the intensity of three selected wavelengths of light. Light-detection assembly 34 includes a single multicolor light-detection array 118 (a 59706 RGB color sensor by Hamamatsu Photonics K.K. (Hamamatsu, Japan)) including 81 light-sensitive elements arranged in a 9×9 array. An on-chip mosaic wavelength filter renders 27 of the light-sensitive elements sensitive to red light (615 nm), 27 sensitive to green light (540 nm) and 27 sensitive to blue light (465 nm). Light-detection array 118 is assembled in device 116 so that all the red-light sensitive elements have a single output 120 to controller 26, all the green-light sensitive elements have a single output 122 to controller 26 and all the blue-light sensitive elements have a single output 124 to controller 26. Consequently, device 116 is configured to determine the intensity of three specified wavelengths of light at substantially the same physical location, the surface of light-detection array 118.

Device 116 is devoid of a wavelength filter 52 associated with detector window 20.

Device 116 comprises an illuminator 32 substantially identical to illuminator 32 of device 108 configured to project light radially outwards through illuminator window 18 in a 360° circumferential section around and perpendicular to axis 12.

The use of device 116 is substantially as described above with reference to device 110, with the changes dictated by the different specified wavelengths of light which intensity is detected.

For example, in some embodiments, an increased intensity of 465 nm light compared to both 540 nm light and 615 nm light relative to normal mucosa is indicative of blood, while a reduced intensity of 540 nm light compared to both 465 nm and 615 nm light compared to normal mucosa is indicative of an invasive adenocarcinoma, see FIG. 1A.

For example, in some embodiments, a reduced intensity of 465 nm and 540 nm light compared to 615 nm light relative to normal mucosa is indicative of an invasive adenocarcinoma or adenoma, while an increased intensity of 465 nm and 540 nm light compared to 615 nm light relative to normal mucosa is indicative of an adenomatous polyp, see FIG. 1B.

In device 116, multicolor light-detection array 118 is an RGB sensor that, due to the low pixel-resolution, is not suitable for imaging. In related embodiments, other multicolor light-detection arrays, including light-detection arrays suitable for imaging, are used in implementing the teachings herein in an analogous manner, that is to say, is configured to provide a single intensity output for each of at least two colors that is a combination (e.g., sum) of the output of multiple discrete light-sensitive elements of the light-detection array. In such related embodiments, any suitable light-detection array technology can be used, e.g., CMOS, CCD or LED arrays.

In light-detection array 118 of device 116, a special RGB filter allows detection of discrete and narrow red, green and blue colors. In related embodiments, any suitable set of colors can be used. For example, light-detection arrays with other RGB filters, for example, Bayer filters, or RGB light-detection arrays such as the Foveon-X3 CMOS light detection array. For example, in some embodiments, a light-detection array is a CYYM light-detection array with three separate outputs: a cyan output, a yellow output and a magenta output. For example, in some embodiments, a light-detection array is an RGBE light-detection array with four separate outputs: a red output, a green output, a blue output and an emerald output. For example, in some embodiments, a light-detection array is an CYGM light-detection array with four separate outputs: a cyan output, a yellow output, a green output and a magenta output. For example, in some embodiments, a light-detection array is an CMYW light-detection array with four separate outputs: a cyan output, a magenta output, a yellow output and a white output (in some embodiments, the white output is not used). For example, in some embodiments, a light-detection array is an RGBW light-detection array with four separate outputs: a red output, a green output, a blue output and a white output (in some embodiments, the white output is not used). In such embodiments, a person skilled in the art is able, upon perusal of the description herein, to decide (for example, with reference to FIGS. 1A, 1B and 1C) which color outputs to compare to provide information indicative of a gastrointestinal abnormality.

EXAMPLES

Example 1

Wavelength Dependence of Diffuse Reflection from Normal and Abnormal Tissue

The wavelength dependence of diffuse reflection from the intestinal abnormalities of blood and invasive adenocarcinoma relative to normal intestinal mucosa was examined in a manner simulating the use of an ingestible device as described herein.

Two freshly excised samples (about 20 cm by 40 cm) of human intestinal tissue were provided, one with a bleeding area and one having an invasive adenocarcinoma, as determined by a pathologist.

As an illuminator, a 0.6 mm diameter glass fiber was connected to an SE NET Model 1-150 fiber optic light source including a 150 Watt Quartz halogen lamp and the distal tip of the fiber contacted with an area of intestinal tissue. As a light-detection assembly, a 0.2 mm diameter glass fiber was connected to a StellarNet Green Fiberoptic spectrometer (StellarNet, Inc, Tampa, Fla., USA) and the distal tip contacted with the intestinal tissue, 0.2 mm from the illuminator glass fiber. As the distal tip of the light detection glass fiber contacted the tissue, only diffusely reflected light was guided into and detected by the spectrometer.

The distal tips of the glass fibers were contacted with a bleeding area of the first sample of intestinal tissue and the spectrometer activated to detect the intensity of light diffusely reflected from the bleeding area from 400 nm to 800 nm at increments of 1 nm. The intensity measurements were repeated with an area of intact mucosa of the same intestinal tissue sample. The relative detected intensities are depicted in FIG. 1A, normalized relative to detected intensities of the intact mucosa, of the intact mucosa (plot 'a') and of the bleeding area (plot 'b').

The distal tips of the glass fibers were contacted with an area of the second sample of intestinal tissue having the invasive adenocarcinoma and the spectrometer activated to detect the intensity of light diffusely reflected from the invasive adenocarcinoma from 400 nm to 800 nm at increments of 1 nm. The intensity measurements were repeated with an area of intact mucosa of the same intestinal tissue sample. The relative detected intensities are depicted in FIG. 1A, normalized relative to detected intensities of the intact mucosa, of the invasive adenocarcinoma (plot 'c').

It is apparent from FIG. 1A, that the diffuse reflection of different tissue types has distinct spectral characteristics, and that the teachings herein may be used to provide information useful for assisting in diagnosis of gastrointestinal abnormalities.

Example 2

Wavelength Dependence of Diffuse Reflection from Normal and Abnormal Tissue

The wavelength dependence of diffuse reflection from various intestinal abnormalities related to invasive adenocarcinoma relative to normal intestinal mucosa were examined in a manner simulating the use of an ingestible device as described herein.

Fifty-four in vivo spectral measurements were performed during standard colonoscopy in patients having various abnormalities as determined by a physician (endoscopist) and confirmed by a pathologist.

As an illuminator, a standard light source (xenon arc lamp) of endoscopic system (Olympus CV180, Olympus, Japan) was used. Light was directed at intestinal tissue to illuminate the entire surface of the tissue. A light-detection assembly includes a 600 g (0.6 mm) diameter glass fiber connected to a StellarNet Green Fiberoptic spectrometer (StellarNet, Inc, Tampa, Fla., USA) as described in Example 1. As the distal tip of the light detection glass fiber contacted the tissue, only diffusely reflected light was guided into and detected by the spectrometer.

For each area of tissue, the distal tip of the light-detection glass fiber was first contacted with an area of an identified intestinal abnormality and the intensity of diffusely reflected light determined between 400 nm and 750 nm at 1 nm increments. The intensity measurements were repeated with an area of intact mucosa of the same intestinal tissue sample. The determined intensities of the abnormal tissue were normalized relative to the determined intensities of the normal tissue.

The relative detected intensities are depicted in FIG. 1B, of intact mucosa (plot 'a'), invasive adenocarcinoma (plot 'c', average of 5 samples), hyperplastic polyp (plot 'd', average of 6 samples), adenomatous polyp (plot 'e', average of 20 samples) and adenoma (plot 'f', average of 23 samples).

It is apparent from FIG. 1B, that the diffuse reflection of different tissue types has distinct spectral characteristics, and that the teachings herein may be used to provide information useful for assisting in diagnosis of gastrointestinal abnormalities.

Example 3

Wavelength Dependence of Diffuse Reflection from Normal and Abnormal Tissue

The wavelength dependence of diffuse reflection from various intestinal abnormalities relative to normal intestinal mucosa was examined in a manner simulating the use of an ingestible device as described herein.

45 freshly excised samples (about 20 cm by 40 cm) of human intestinal tissue were provided, having various abnormalities as determined by a pathologist.

As an illuminator, a quartz halogen lamp with polarizing filter was directed at a sample of intestinal tissue to illuminate the entire surface of the tissue. A spectral camera (SD-300 from Applied Spectral Imaging, Migdal Haemek, Israel) with a polarizing filter oriented perpendicularly to the polarizing filter of the illuminator was used as a light-detection assembly with the objective lens positioned 10 cm from a tissue sample surface to acquire spectra using the polarized-gated method between 400 nm and 800 nm at increments of 1 nm of areas of the surface of each of the samples. As the illuminator and light-detection assembly were cross-polarized, the light detected was primarily diffusely reflected light.

The spectra of areas of abnormal tissue corresponding to bleeding tissue (11 samples), invasive adenocarcinoma (5 samples), hyperplastic polyps (6 samples) and adenoma (23 samples) were normalized relative to the spectra of nearby normal tissue from the same sample.

The spectra of each of the abnormal tissue types and the normal tissue were averaged and displayed in FIG. 1C: normal tissue (plot 'a', average of 45 spectra), bleeding (plot 'b', average of 11 spectra) invasive adenocarcinoma (plot 'c', average of 5 spectra), hyperplastic polyps (plot 'd', average of 6 spectra) and adenoma (plot 'f', average of 23 spectra).

It is apparent from FIG. 1C, that the diffuse reflection of different tissue types has distinct spectral characteristics, and that the teachings herein may be used to provide information useful for assisting in diagnosis of gastrointestinal abnormalities.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

For example, in the embodiments described above, the devices comprise an illuminator with a radial diffuser giving a homogenous illumination around the device. In some embodiments, other types of illuminators are used, for example, illuminating strips or a circular array of outwardly-facing light sources such as LEDs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Citation or identification of any reference in this application shall not be construed as an admission that such reference is available as prior art to the invention.

Section headings are used herein to ease understanding of the specification and should not be construed as necessarily limiting.

The invention claimed is:

1. An ingestible device useful for providing information useful for diagnosis of a gastrointestinal abnormality, said ingestible device comprising:
   a) an ingestible casing having a device axis, a body section, a distal end and a proximal end;
   b) inside said casing, an illuminator configured to project light radially outwards through an illuminator window of said casing simultaneously in a 360° circumferential section around said device axis;
   c) inside said casing, at least one light-detection assembly configured to perform a measurement of intensities of at least two different specified wavelengths of light projected by said illuminator and passing through an associated detector window simultaneously in a 360° circumferential section around said device axis, after reflection from a 360° circumferential section of a gastrointestinal tract, without acquiring an image; and
   d) inside said casing, a controller configured to compare variations in said intensities of said at least two different specified wavelengths reflected from said gastrointestinal tract from said at least one light-detection assembly, wherein:
   at least one of said at least two different specified wavelengths is a reference wavelength,
   at least one of said at least two different specified wavelengths is a diagnostic wavelength, at which intensity changes are indicative of said abnormality,
   said controller is configured to distinguish between (a) data taken during relative motion of said ingestible device with respect to walls of said gastrointestinal tract, and (b) data taken due to light reflecting off said abnormality, by identifying whether a reduction in intensity of said diagnostic wavelength is accompanied by a reduction in intensity of said reference wavelength,
   said controller, by the comparing of said variations in said intensities of said at least two different specified wavelengths, is configured to (1) provide an indication of contact of said ingestible device with said walls of said gastrointestinal tract, and, during said measurement (2) provide said information useful for diagnosis of said gastrointestinal abnormality,
   in a first determination, said controller is configured to provide an indication of no contact with said walls of said gastrointestinal tract, when said controller detects a similar magnitude of reduction in intensity of reflection of both said reference wavelength and said diagnostic wavelength, and
   in a second determination, said controller is configured to provide an indication of contact with said walls of said gastrointestinal tract and said abnormality, when said controller detects a reduction in intensity of reflection of said diagnostic wavelength while detecting that the intensity of reflection of said reference wavelength remains constant.

2. The device of claim 1, wherein said at least one light-detection assembly and said associated detector window comprise at least one wavelength filter configured to pass only light having at least one of said at least two different specified wavelengths of light.

3. The device of claim 1, wherein said at least one light-detection assembly comprises a single said light-detection assembly.

4. The device of claim 1, wherein said at least one light-detection assembly comprises at least two said light detection assemblies.

5. The device of claim 1, wherein said device is configured to perform said measurements of said at least two different specified wavelengths of light each at a different location in the device.

6. The device of claim 1, wherein said device is configured to perform said measurements of said at least two different specified wavelengths of light each with a different light-detection assembly.

* * * * *